US008344022B2

(12) United States Patent
Villanueva et al.

(10) Patent No.: US 8,344,022 B2
(45) Date of Patent: Jan. 1, 2013

(54) VAGINAL HEALTH PRODUCTS

(75) Inventors: Julie M. Villanueva, Decatur, GA (US);
Sohail Malik, Athens, GA (US)

(73) Assignee: Kimberly-Clark Worldwide, Inc.,
Neenah, WI (US)

( * ) Notice: Subject to any disclaimer, the term of this patent is extended or adjusted under 35 U.S.C. 154(b) by 387 days.

(21) Appl. No.: 12/364,673

(22) Filed: Feb. 3, 2009

(65) Prior Publication Data

US 2009/0203772 A1     Aug. 13, 2009

Related U.S. Application Data

(62) Division of application No. 10/872,194, filed on Jun. 17, 2004, now Pat. No. 7,485,666.

(51) Int. Cl.
A01N 43/16    (2006.01)
A01N 35/00    (2006.01)
A01N 33/08    (2006.01)
A01N 43/08    (2006.01)
A61K 31/355   (2006.01)
A61K 31/12    (2006.01)
A61K 31/13    (2006.01)
A61K 31/34    (2006.01)

(52) U.S. Cl. ......... 514/458; 514/690; 514/667; 514/470

(58) Field of Classification Search .................. 514/458, 514/690, 667, 470
See application file for complete search history.

(56) References Cited

U.S. PATENT DOCUMENTS

| | | |
|---|---|---|
| 2,798,055 A | 7/1957 | Brown |
| 2,831,854 A | 4/1958 | Tucker et al. |
| 3,963,699 A | 6/1976 | Rizzi et al. |
| 4,005,195 A | 1/1977 | Jandacek |
| 4,005,196 A | 1/1977 | Jandacek et al. |
| 4,051,842 A | 10/1977 | Hazel et al. |
| 4,140,122 A | 2/1979 | Kuhl et al. |
| 4,383,529 A | 5/1983 | Webster |
| 4,509,949 A | 4/1985 | Huang et al. |
| 4,517,360 A | 5/1985 | Volpenhein |
| 4,518,614 A * | 5/1985 | Parkinson .................. 514/18.8 |
| 4,518,772 A | 5/1985 | Volpenhein |
| 4,599,379 A | 7/1986 | Flesher et al. |
| 4,603,146 A * | 7/1986 | Kligman .................. 514/559 |
| 4,628,078 A | 12/1986 | Glover et al. |
| 4,677,120 A | 6/1987 | Parish et al. |
| 4,702,913 A * | 10/1987 | Marty ..................... 424/579 |
| 4,797,300 A | 1/1989 | Jandacek et al. |
| 4,835,206 A | 5/1989 | Farrar et al. |
| 4,847,071 A | 7/1989 | Bissett et al. |
| 4,849,484 A | 7/1989 | Heard |
| 4,885,311 A | 12/1989 | Parish et al. |
| 4,937,370 A | 6/1990 | Sabatelli |
| 4,962,091 A | 10/1990 | Eppstein et al. |
| 4,976,953 A | 12/1990 | Orr et al. |
| 4,999,186 A | 3/1991 | Sabatelli et al. |
| 5,049,584 A | 9/1991 | Purcell et al. |
| 5,087,445 A | 2/1992 | Haffey et al. |
| 5,100,660 A | 3/1992 | Hawe et al. |
| 5,124,356 A | 6/1992 | Purcell et al. |
| RE34,075 E | 9/1992 | Purcell et al. |
| 5,151,425 A | 9/1992 | Clark |
| 5,306,515 A | 4/1994 | Letton et al. |
| 5,306,516 A | 4/1994 | Letton et al. |
| 5,364,617 A | 11/1994 | Bush et al. |
| 5,487,884 A | 1/1996 | Bissett et al. |
| 5,487,899 A | 1/1996 | Davis |
| 5,607,980 A | 3/1997 | McAtee et al. |
| 5,681,852 A | 10/1997 | Bissett |
| 5,686,082 A | 11/1997 | N'Guyen |
| 5,686,367 A | 11/1997 | Hayashi |
| 5,789,391 A | 8/1998 | Jacobus et al. |
| 5,821,250 A | 10/1998 | Wu et al. |
| 5,837,861 A | 11/1998 | Pendergast et al. |
| 5,958,897 A | 9/1999 | Jacobus et al. |
| 5,972,904 A | 10/1999 | Jacobus et al. |
| 5,972,957 A | 10/1999 | Wu et al. |
| 5,981,506 A | 11/1999 | Jacobus et al. |
| 5,981,547 A | 11/1999 | Wu et al. |
| 5,985,849 A | 11/1999 | Kindon et al. |
| 5,997,887 A | 12/1999 | Ha et al. |
| 6,107,091 A | 8/2000 | Cowsert |
| 6,107,297 A | 8/2000 | Kindon et al. |
| 6,121,317 A | 9/2000 | Wu et al. |
| 6,200,981 B1 | 3/2001 | Kindon et al. |
| 6,242,491 B1 * | 6/2001 | Kaddurah-Daouk ......... 514/565 |
| 6,264,975 B1 | 7/2001 | Boucher, Jr. |
| 6,277,855 B1 | 8/2001 | Yerxa |
| 6,437,003 B1 | 8/2002 | Roullet et al. |
| 6,437,129 B1 | 8/2002 | Teng et al. |

(Continued)

FOREIGN PATENT DOCUMENTS

EP     0228868 A2     7/1987

(Continued)

OTHER PUBLICATIONS

European Communication and Search Report for EP Application No. 03799944.8, mailed Jan. 10, 2007, 4 pgs.
International Preliminary Report on Patentability for PCT Application No. PCT/US2005/020286, mailed Jan. 4, 2007, 6 pgs.
International Search Report for PCT Application No. PCT/US03/32362, mailed Jun. 22, 2004, 1 pg.
International Search Report for PCT/US03/40157, mailed Aug. 26, 2004, 6 pgs.
International Search Report for corresponding PCT Application No. PCT/US2005/020286 (Oct. 27, 2005), 5 pgs.
Prosecution File History for U.S. Appl. No. 10/320,730, issued as U.S. Patent No. 7,098,189, 136 pgs, Oct. 2007.
Written Opinion for corresponding PCT Application No. PCT/US2005/020286, mailed Nov. 3, 2005, 8 pgs.
Barrio, Jorge R., et al., "Fluorescent Adenosine and Cytidine Derivatives", Biochemical and Biophysical Research Communications, 46(2), (1972), 597-604.

(Continued)

*Primary Examiner* — Sreeni Padmanabhan
*Assistant Examiner* — Kendra D Carter
(74) *Attorney, Agent, or Firm* — Dority & Manning, P.A.

(57) ABSTRACT

The invention provides compositions and methods for increasing cell growth, stimulating cell turnover and promoting the secretion of mucus within the reproductive tract of a female mammal.

8 Claims, 6 Drawing Sheets

U.S. PATENT DOCUMENTS

| | | |
|---|---|---|
| 6,537,527 B1 | 3/2003 | Kvalnes et al. |
| 7,098,189 B2 | 8/2006 | Malik |
| 7,179,481 B2 | 2/2007 | Villanueva |
| 7,258,878 B2 | 8/2007 | Greene et al. |
| 2003/0206893 A1 | 11/2003 | Malik |
| 2004/0029839 A1 | 2/2004 | Boulle et al. |
| 2004/0116511 A1 | 6/2004 | Malik |

FOREIGN PATENT DOCUMENTS

| | | |
|---|---|---|
| EP | 1333021 A2 | 8/2003 |
| JP | 58103307 | 6/1983 |
| WO | WO 9108751 A1 | 6/1991 |
| WO | WO 9116034 A1 | 10/1991 |
| WO | WO 9116035 A1 | 10/1991 |
| WO | WO 9306792 A1 | 4/1993 |
| WO | WO 9407529 A1 | 4/1994 |
| WO | WO 9415621 A1 | 7/1994 |
| WO | WO 9523780 A2 | 9/1995 |
| WO | WO 9534280 A1 | 12/1995 |
| WO | WO 9620703 A1 | 7/1996 |
| WO | WO 9954507 A1 | 10/1999 |
| WO | WO 0032757 A2 | 6/2000 |
| WO | WO 0077235 A1 | 12/2000 |
| WO | WO 0102600 A2 | 1/2001 |
| WO | WO 0114872 A1 | 3/2001 |
| WO | WO 0242440 A2 | 5/2002 |
| WO | WO 02060506 A1 | 8/2002 |
| WO | WO 02080890 A2 | 10/2002 |
| WO | WO 02085248 A2 | 10/2002 |
| WO | WO 03094907 A1 | 11/2003 |
| WO | WO 2004058151 A2 | 7/2004 |
| WO | WO 2004060394 A1 | 7/2004 |
| WO | WO 2006007337 A1 | 1/2006 |

OTHER PUBLICATIONS

Biernat, J., et al., "New Observations Concerning the Chloroacetaldehyde Reaction With Some tRNA Constituents. Stable Intermediates, Kinetics and Selectivity of the Reaction", Nucleic Acids Research, 5(3), (1978), 789-804.

Blackburn, G. M., et al., "The Synthesis and Metal Binding Characteristics of Novel, Isopolar Phosphonate Analogues of Nucleotides", Journal of the Chemical Society, Perkins Transactions I, (1984), 1119-1125.

Clark, E. A., et al., "Integrins and Signal Transduction Pathways: The Road Taken", Science, 268, (1995), 233-239.

Cussack, N. J., et al., "Subtypes of $P_2$-Purinoceptors. Studies Using Analogues of ATP", Annals of the New York Academy of Sciences, 603(1), (1990), 172-181.

Eckert, R. L., et al., "The Epidermal Keratinocyle as a Model for the Study of Gene Regulation and Cell Differentiation", Physiologial Reviews, 77(2), (1997), 397-424.

Eckstein, Fritz, et at., "Synthesis and Properties of Diastereoisomers of Adenosine 5'-(O-1-Thiotriphosphate) and Adenosine 5'( O-2-Thiotriphosphate)", Biochemistry, 15(8), (1976),1685-1691.

Fischer, Bilha, et al., "Identification of Potent, Selective $P_{2y}$-Purinoceptor Agonists: Structure-Activity Relationships for 2-Thioether Derivatives of Adenosine 5'-Triphosphate", J. Med. Chem., 36, (1993), 3937-3946.

Garrad, Richard C., "Structural Basis of Agonist-induced Desensitization and Sequestration of the $P2Y_2$ Nucleotide Receptor", Journal of Biological Chemistry, 273(45). (Nov. 6, 1998), 29437-29444.

Giuliano, Anna R., et al., "Antioxidant Nutrients: Associations With Persistent Human Papillomavirus Infection", Cancer Epidemiology, Biomarkers & Prevention, 6, (1997), 917-923.

Goody, R. S., et al., Thiophosphate Analogs of Nucleoside Di- and Triphosphates, Journal of the American Chemical Society, 93(23), (Nov. 17, 1971), 6252-6257.

Gorodeski, George I., "Regulation by Retinoids of $P2Y_2$ Nucleotide Receptor mRNA in Human Uterine Cervical Cells", American Journal of Physiology, 275, (1998), C758-C765.

Grove, Gary L., et al., "Age-Associated Changes in Human Epidermal Cell Renewal", Journal of Gerontology, 38(6), (1983), 137-142.

Hale, William E., et al., "Vitamin E Effect on Symptoms and Laboratory Values in the Elderly", Journal of The American Dietetic Association, 86(5), (1986), 625-629 .

Hall, Ross H., et al., "Nucleoside Polyphosphates. II.. A Synthesis of Uridine-5'-di- and Triphosphate", Journal of the American Chemistry Society, 76, (Oct. 20, 1954), 5056-5060.

Hoard, Donald E., et al., "Conversion of Mono- and Oligodeoxyribonucleotides", Journal of the American Chemical Society, 87(8), (1965), 1785-1788.

Jansen, L. H., et al., "Improved Fluorescence Staining Technique for Estimating Turnover of the Human Stratum Corneum", British Journal of Dermatology, 90(1), (1974), 9-12.

Kayasuga-Mikado, Kikuko, et al., "Modification of Adenine and Cytosine Derivatives With Bromoacetaldehyde", Chemical & Pharmaceutical Bulletin, 28(3),_(1980), 932-938.

Kenner, G. W., et al., "Nucleotides. Part XXVIII. A Synthesis of Uridine-5' Triphosphate (UTP)", Journal of the Chemical Society, Part II, (1954), 2288-2293.

Kochetkov, N. K., et al., "New Reaction of Adenine and Cytosine Derivatives, Potentially Useful for Nucleic Acids Modification", Tetrahedron Letters, 12(22), (1971), 1993-1996.

Kwasniewska, Anna, et al., "Content of α-Tocopherol in Blood Serum of Human *Papillomavirus*-Infected Women With Cervical Dysplasias", Nutrition and Cancer, 28(3), (1997), 248-251.

Ledee-Bataille, N., et al., "Combined Treatment by Pentoxifylline and Tocopherol for Recipient Women With a Thin Endometrium Enrolled in an Oocyte Donation Programme", Human Reproduction, 17(5), (2002), 1249-1253.

Li-Weber, Min, et al., "Vitamin E Inhibits CD95 Ligand Expression and Protects T Cells From Activation-Induced Cell Death", The Journal of Clinical Investigation, 110(5), (2002), 681-690.

Ludwig, Janos, et al., "Rapid and Efficient Synthesis of Nucleoside 5'-O- (1-Thiotriphosphate), 5'-Triphosphates and 2'.3'-Cyclophosphorothioates Using 2-Chloro-4$H$-1,3,2-benzodioxaphosphorin-4-one", Journal of Organic Chemistry, 54(3),_(1989), 631-635.

Mass-Szabowski, N. ,et al., "lnterleukin-1-Induced Growth Factor Expression in Postmitotic and Resting Fibroblasts", The Journal of Cell Biology, 122(2). (1993), 417-429.

Moffatt, J. G., et al., "Nucleoside Polyphosphates. X. The Synthesis and Some Reactions of Nucleoside-5' Phosphoromorpholidates and Related Compounds. Improved Methods for the Preparation of Nucleoside-5' Polyphosphates", Journal of the American Chemical Society, 83(3), (1961), 649-658.

Myers, Terrell C., et al., "Phosphonic Acid Analogs of Nucleoside Phosphates. I. The Synthesis of 5'-AdenylylMethylenediphosphonate, a Phosphonic Acid Analog of ATP", Journal of The American Chemical Society, 85, (1963), 3292-3295.

Ng, Kam-Mui E., et al., "The Action of a Water-Soluble Cardodimide on Adenosine-5'-polyphosphates", Nucleic Acids Research, 15(8), (1987), 3573-3580.

Oikarinen, A., "The Aging of Skin: Chronaging Versus Photoaging", Photodermatol. Photoimmunol. Photomed., vol. 1, (1990), 3-4.

Rapaport, Eliezer, et al., "HeLa Cell DNA Polymerase α is Tightly Associated with Tryptophanyl-tRNA Synthetase and Diadenosine 5',5'''-$P^1$, $P^4$-tetraphosphase Binding Activities, Proc. Natl. Acad. Sci. USA 78(2), (1981), 838-842.

Ridge, B. D., et al., "The Dansyl Chloride Technique for Stratum Corneum Renewal as an Indicator of Changes in Epidermal Mitotic Activity Following Topical Treatment", British Journal of Dermatology, 118, (1988) 167-174.

Rock, Cheryl L., et al., "Prevention of Cervix Cancer", Critical Reviews in Oncology/Hematology, 33(3), (2000), 169-185.

Secrist, III, John A.., et al., "Fluorescent Modification of Adenosine-Containing Coenzymes. Biological Activities and Spectroscopic Properties", Biochemistry, 11(19), (1972), 3499-3506.

Smola, H., et al., "Mutual Induction of Growth Factor Gene Expression by Epidermal-Dermal Cell Interaction", The Journal of Cell Biology, 122(2), (1993), 417-429.

Trompezinski, S., et al., "UV Radiation and Prostaglandin E2 Up-Regulate Vascular Endothelial Growth Factor (VEGF) in Cultured Human Fibroblasts", Inflammation Research, 50, (2001), 422-427.

Vallejo, Carmen G., et al., "Dinucleosidasetetraphosphatase in Rat Liver and *Artemia salina*", Biochimica et Biophysica Acta (BBA)—Enzymology, 438(1), (1976), 304-309.

Yoshikawa, M., et al., "Studies of Phosphorylation. III. Selective Phosphorylation of Unprotected Nucleosides", Bulletin of the Chemical Society of Japan, 42(12), (1969), 3505-3508.

Yoshikawa, Masaharu, et al., "A Novel Method for Phosphorylation of Nucleosides to 5'-Nucleotides", Tetrahedron Letters, 8(50), (1967), 5065-5068.

* cited by examiner

SEQUENCE LISTING

```
<160> NUMBER OF SEQ ID NOS: 6

<210> SEQ ID NO 1
<211> LENGTH: 20
<212> TYPE: DNA
<213> ORGANISM: Homo sapiens

<400> SEQUENCE: 1
tgtcttcgcc ctctgcttcc                                               20

<210> SEQ ID NO 2
<211> LENGTH: 20
<212> TYPE: DNA
<213> ORGANISM: Homo sapiens

<400> SEQUENCE: 2
gtcaggccag gggtgtcatt                                               20

<210> SEQ ID NO 3
<211> LENGTH: 20
<212> TYPE: DNA
<213> ORGANISM: Homo sapiens

<400> SEQUENCE: 3
agtcggttgg agcgagcatc                                               20

<210> SEQ ID NO 4
<211> LENGTH: 20
<212> TYPE: DNA
<213> ORGANISM: Homo sapiens

<400> SEQUENCE: 4
gggcacgaag gctcatcatt                                               20

<210> SEQ ID NO 5
<211> LENGTH: 20
<212> TYPE: DNA
<213> ORGANISM: Homo sapiens

<400> SEQUENCE: 5
agcccaggac tgtggtctgc                                               20

<210> SEQ ID NO 6
<211> LENGTH: 20
<212> TYPE: DNA
<213> ORGANISM: Homo sapiens

<400> SEQUENCE: 6
gctcacgttc agggctgtca                                               20
```

VAGINAL HEALTH PRODUCTS

RELATED APPLICATIONS

The present application is a divisional of U.S. application Ser. No. 10/872,194, filed on Jun. 17, 2004, which is incorporated herein in its entirety by reference thereto.

FIELD OF THE INVENTION

The present invention relates to the use of vitamin E and various plant hormones for increasing the growth, renewal and mucus production of vaginal epithelial cells and improving the health of the female genital tract.

BACKGROUND OF THE INVENTION

As estrogen levels fall during menopause, estrogen dependent tissue will start to involute and take on the characteristic appearance of estrogen deprivation. Cervical mucus levels diminish and vaginal mucosa regresses during menopause. With aging, the vagina becomes shortened, ruggae disappear, and elasticity is lost. Vaginal secretion becomes scanty. When estrogen is provided, some of these effects are reversed: the cervix may secrete more mucus and the vaginal mucosa may regain lost layers. However, the symptoms often do not disappear completely, in part because the amount of estrogen provided for hormone replacement is lower than circulating estrogen levels during a normal menstrual cycle.

Approximately 40% of postmenopausal women experience atrophic vaginitis or vaginal dryness. During vaginal atrophy, the vaginal epithelium decreases in thickness, hydration, rugae (folds), and blood flow. Causes of atrophic vaginitis include a decrease in the amount of estrogen present both locally and systemically as well as environmental factors such as chemotherapy, antihistamines, smoking cigarettes, excessive exercise, and perineal products (i.e. douches, deodorants, and perfumes). Estrogens or hormone replacement therapies (HRTs) are effective in reducing vaginal dryness. However, possible dangerous side effects include a higher incidence of breast cancer, endometrial cancer, blood clots, nausea, breast tenderness, and headache.

Products that are available over-the-counter include lubricants such as Astroglide and KY Lubricating Jelly as well as moisturizers such as Replens and KY Long Lasting Moisturizer. These products, which are mostly water in composition, provide only temporary relief (1-2 days) for symptoms and provide virtually no long-term benefits to the vaginal tissue.

Therefore, vaginal dryness and regression of vaginal mucosa are problematic, particularly after menopause. Stimulation of cervical mucus production can help alleviate vaginal dryness, and can also augment the action of exogenously administered estrogen to alleviate vaginal dryness. Moreover compositions and methods for counteracting the regression of vaginal mucosa are also needed.

SUMMARY OF THE INVENTION

The invention provides non-hormonal therapies for treating certain reproductive and vaginal problems, including atrophic vaginitis. In general, these therapies have minimal side effects, stimulate natural and non-hormonal mechanisms of action, promote vaginal cell growth and renewal, increase mucus secretion, stimulate gene expression, replace aging tissues with new tissues and maintain or restore healthy tissue function.

Thus, the present invention is directed to a variety of compositions and methods for treating or preventing vaginal and/or reproductive problems in a female mammal. The compositions involve an effective amount of a composition that includes vitamin E and/or a plant hormone such as jasmonic acid or gibberellic acid. The compositions of the invention can also include a retinoid or carotenoid (e.g. vitamin A) and/or one or more nucleotide(s) or nucleoside(s). In general, these compositions can be administered topically or intravaginally. The compositions and methods of the invention can inter alia increase vaginal cell growth, stimulate renewal or turnover of vaginal cell layers, and/or to alleviate or diminish vaginal dryness in a female mammal. The compositions and methods of the invention can also stimulate the production of collagen and fibronectin.

In one embodiment, the invention provides a method to increase growth of vaginal or cervical epithelial cells by administering to the female mammal an effective amount of vitamin E and/or a plant hormone such as jasmonic acid or gibberellic acid. The compositions of the invention can also include a retinoid or carotenoid (e.g. vitamin A) and/or one or more nucleotide(s) or nucleoside(s).

In another embodiment, the invention provides a method to increase expression of mucin, for example, mucin-4, in vaginal or cervical epithelial cells by administering to the female mammal a composition having an effective amount of vitamin E and/or a plant hormone such as jasmonic acid or gibberellic acid. The compositions of the invention can also include a retinoid or carotenoid (e.g. vitamin A) and/or one or more nucleotide(s) or nucleoside(s).

In another embodiment, the method involves increasing the expression of $P2Y_2$ receptors or estrogen receptors or vascular endothelial growth factor in vaginal or cervical epithelial cells by administering to the female mammal a composition having an effective amount of vitamin E and/or a plant hormone such as jasmonic acid or gibberellic acid. The compositions of the invention can also include a retinoid or carotenoid (e.g. vitamin A) and/or one or more nucleotide(s) or nucleoside(s).

Such methods can facilitate renewal of regressing vaginal mucosa, prevent or treat vaginal dryness in a mammal, or maintain or enhance the normal protective function of vaginal mucus in a mammal. In general, the vitamin E, a plant hormone (e.g. jasmonic acid or gibberellic acid) and other compounds are administered intravaginally.

DESCRIPTION OF THE FIGURES

FIG. 2A graphically illustrates the effects of 10 μM trans-retinoic acid (circles), 9-cis-retinoic acid (squares), and 13-cis-retinoic acid (diamonds) on ME-180 cell growth over a period of two days. FIG. 2B graphically illustrates the effects of 1 μM trans-retinoic acid (circles), 9-cis-retinoic acid (squares), and 13-cis-retinoic acid (diamonds) on ME-180 cell growth over a period of two days. FIG. 2C graphically illustrates the effects of 100 nM trans-retinoic acid (circles), 9-cis-retinoic acid (squares), and 13-cis-retinoic acid (diamonds) on ME-180 cell growth over a period of two days. The number of ME-180 cells is provided on the y-axes.

DETAILED DESCRIPTION OF THE INVENTION

Figure 1:
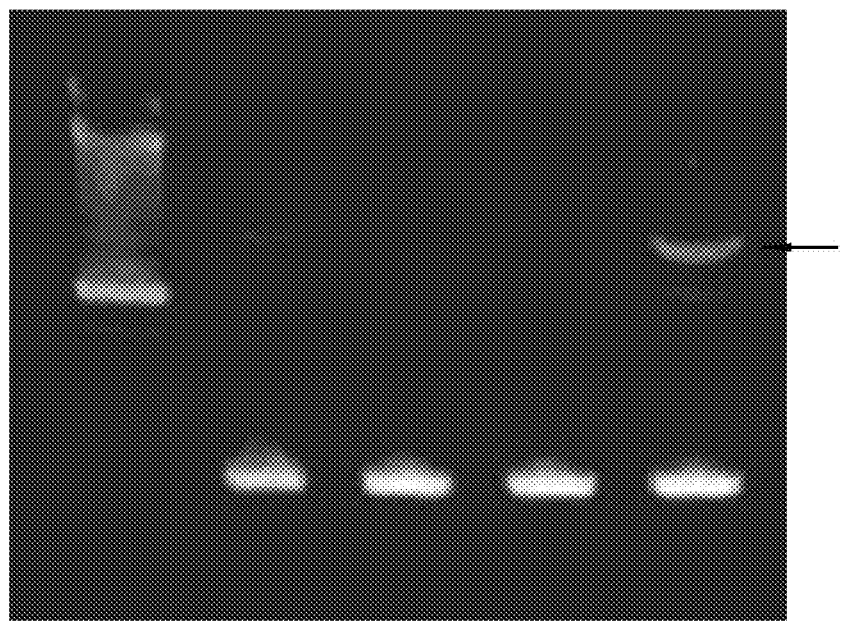
FIG. 1 illustrates that 1 μM vitamin E for 24 hours increases mucin-4 expression. An ethidium stained 2.0% agarose gel is shown with separated β-actin (350 bp positive control) and mucin-4 (800 bp) PCR products. Lane 1 contains a DNA marker. Lanes 2-5 contain PCR products using cervical cDNA, placenta cDNA, ME-180 cDNA (no treatment), and ME-180 cDNA (1 μM vitamin E), respectively, as templates.

The invention provides compositions and methods for increasing the secretion of mucus, and stimulating cell growth and renewal of epidermal layers within the reproductive system of a female mammal. The compositions of the invention include vitamin E and/or a plant hormone such as jasmonic acid or gibberellic acid. Administration of such compositions can increase mucus production, stimulate cell growth and promote the renewal of vaginal and cervical cells in the female reproductive system. Thus, the compositions of the invention can facilitate replacement of older cells with new cells, thereby rejuvenating the lining of the female reproductive tract.

This invention utilizes inexpensive, readily available active compounds that effectively enhance the natural ability of vaginal and cervical tissues to renew themselves and to produce moisture. The methods and compositions of the invention therefore avoid strong chemicals and unnatural substances whose effects on the health and reproduction of the user are unknown.

The methods of the invention may improve the quantity and quality of the secretions of the reproductive organs, repair and replace aging tissues and influence expression of genes within reproductive, epithelial and mucosal cells. Genes whose expression may be influenced by the methods of the invention include mucin genes.

Mucins refer to a family of glycoproteins of high molecular weight, secreted or expressed by goblet and nongoblet epithelial cells of mucosal tissues. Mucins can form mucus, a highly hydrated gel of particular structure and function. Mucins from diverse species have similar structural features, particularly with regard to the mucin protein backbone. Nine distinct mucin genes have been identified (MUC1, 2, 3, 4, MUC5AC, MUC5B, MUC6, 7 and 8). Mucins are glycoproteins containing from fifty to eighty percent carbohydrate. They are large, elongated molecules (molecular weight $10^5$ to $10^7$ daltons) with a protein backbone to which oligosaccharides are attached in a bottle-brush configuration. The oligosaccharide side chains, or bristles, can be highly variable in their make-up, indicating that the more basic functions of the molecule derive from the protein core. These molecules can be crosslinked through disulfide bridges to form very high molecular weight gels. Different tissues may produce different types of mucins.

According to the invention, vitamin E can increase the expression of mucins and thereby provide increased secretion and formation of mucus within the reproductive tracts of female mammals.

Influences on mucus secretion that may be provided by the invention include, but not limited to, the quantity and type of mucin (e.g. sulfo and/or sialomucin), changes in viscosity, hydrogen ion retardation, hydrophobicity, changes in phospholipid content, glycosylation and sulfation, macromolecular assembly, surface tension, adhesivity, transport properties, elastic modulus, tensile properties, rigidity factors, recoil factors, spinnbarkeit, sperm penetration qualities, consistency, cellularity, ferning, and the like.

The methods of the invention can change the constitutive and stimulated secretions of the local reproductive system, including those of the vagina, cervix, uterus, fallopian tube, Bartholin or vestibular glands and urethral secretions. The methods and compositions of the invention can influence the function of the mucus genes found in the reproductive system, including, but not limited to genes that control mucus production in the cervix, uterus, and Bartholin's glands and other parts of the reproductive system with mucus secreting cells. The squamous epithelium of the lower genital tract (vagina; for example) and epithelial cells of the cervix can be treated by the methods of the invention. Included are methods to influence or change the secretary effects of the mucus genes, mucus secreting cells and cells that influence the properties of secretory and cell surface mucins of all the above mentioned glands of the reproductive system.

Mucus can be defined by its chemical, physical and biological properties. Rheological or flow properties of mucus include viscosity, rate of flow, shear index, spinnbarkeit or stretch of mucus due to increased viscoelasticity and ferning (crystallization) parameters. Changing or stimulating the hydration, viscosity, quantity or other properties of vaginal secretions can influence a variety of conditions and disorders, including, but not limited to contraception, infertility, menopause, dyspareunia, infections, and others related and unrelated conditions. Description of the function and anatomy of these organs can be found in Novak's Gynecology, 12.sup.th edition, eds. Berek, Adashi and Hillard, Williams and Wilkins, Baltimore, Md., 1996.

The methods and compositions of the invention can also increase the growth of cells lining the female reproductive tract, for example, vaginal and cervical cells. Such increased cell growth may occur very quickly, or after only a few days of treatment. For example, after only two or three days of treatment the number of newly formed cells can be almost twice or almost three times or four times or five times that of untreated individuals. As treatment progresses the number of newly formed cells can increase further. For example, treated individuals may have about 2 to about 20 times the number of young, newly formed cells compared to untreated individuals. Other individuals may have about 2 to about 10 times the number of young, newly formed cells as untreated individuals. Such increased cell growth can repair and replace aging cells and tissue, rejuvenate the lining of the female reproductive tract and provide greater resilience and improved health to tissues involved in reproduction.

The invention therefore has at least two general utilities. First, the invention may increase the amount of mucus and/or the water content of secretions of the reproductive organs to improve the health and to increase lubrication of the female reproductive system. Second, the invention may be used to rejuvenate aging tissues and enhance the health and resiliency of those tissues, for example, by stimulating cellular growth, gene expression and mucus secretion.

Vitamin E

There are at least eight naturally occurring compounds with vitamin E activity. Each vitamin E compound is a derivative of 6-chromanol. See ULLMANN'S ENCYCLOPEDIA OF INDUSTRIAL CHEMISTRY, Vol. A 27, *Vitamin E*, Chapter 4: 478-488 (VCH Verlagsgesellschaft, 1996). The tocopherol group (Compounds Ia-d) has a saturated side chain, while the tocotrienol group (Compounds IIa-d) has an unsaturated side chain. The tocopherol group comprises compounds of formula I:

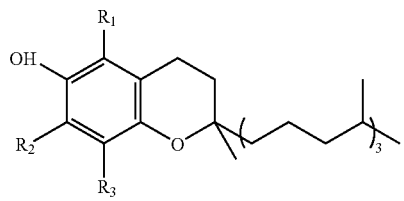

I wherein $R_1$, $R_2$ and $R_3$ are all separately hydrogen (H), methyl ($CH_3$) or hydroxyl (OH). The compound α-tocopherol (Ia) is a compound of formula I, wherein $R_1$, $R_2$ and $R_3$ are all methyl. The compound β-tocopherol (Ib) is a compound of formula I, wherein $R_1$ and $R_3$ are methyl and $R_2$ is hydrogen. The compound γ-tocopherol (Ie) is a compound of formula I, wherein $R_1$ is hydrogen, while $R_2$ and $R_3$ are methyl. The compound δ-tocopherol (Id) is a compound of formula I, wherein $R_1$ and $R_2$ are hydrogen, while $R_3$ is methyl.

The tocotrienol group comprises compounds of formula II:

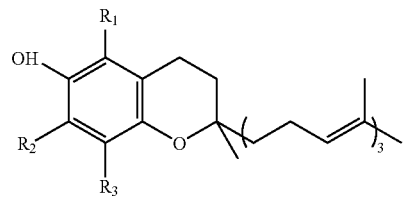

wherein $R_1$, $R_2$ and $R_3$ are all separately hydrogen (H), methyl ($CH_3$) or hydroxyl (OH). The compound α-tocotrienol (IIa) is a compound of formula II, wherein $R_1$, $R_2$ and $R_3$ are all methyl. The compound β-tocotrienol (IIb) is a compound of formula II, wherein $R_1$ and $R_3$ are methyl and $R_2$ is hydrogen. The compound γ-tocotrienol (IIc) is a compound of formula II, wherein $R_1$ is hydrogen, while $R_2$ and $R_3$ are methyl. The compound δ-tocotrienol (IId) is a compound of formula II, wherein $R_1$ and $R_2$ are hydrogen, while $R_3$ is methyl Within the present invention, vitamin E is understood to include all of the above mentioned tocopherols and tocotrienols with vitamin E activity.

When present in the compositions of the present invention, vitamin E compounds can be used in an amount of about 0.0001% to about 50%, or from about 0.001% to about 20%, or from about 0.001% to about 10%, or from about 0.01% to about 5%, or from about 0.05% to about 2% of the composition. According to the invention, in situ concentrations of an active gibberellic acid ranging from about $10^{-5}$ M to about $10^{-7}$ M are effective for increasing epithelial cell proliferation and mucin-4 expression.

Gibberellic Acid

Gibberellic acid comprises a class of compounds that is also referred to as gibberellins. Gibberellins are plant hormones that affect a wide variety of processes throughout the life cycle of plants, including seed germination, stem elongation, flower induction, anther development, and seed and pericarp growth. Gibberellins are tetracyclic diterpenoid acids that can isolated from fungi and higher plants and that have the ent-gibberellane ring system shown in the following structure (III).

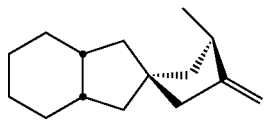

Gibberellins were first isolated by Japanese researchers in the 1930s from cultures of the fungus *Gibberella fujikuroi* (*Fusarium moniliforme*). Gibberellins are secondary metabolites that have since been shown to be present in other fungal species, in some ferns, and in many gymnosperms and angiosperms. Of the 121 known gibberellins, 96 have been identified only in higher plants, 12 are present only in *Gibberella*, and 12 are present in both. As observed in *Gibberella*, many different gibberellins can be present in individual angiosperms.

Two main types of gibberellins exist: the $C_{20}$-gibberellins, which have 20 carbon atoms (structure IV, below), and the $C_{19}$-gibberellins, in which the twentieth carbon atom has been lost due to metabolism (structure V, below). The carboxylic acid at carbon-19 bonds to carbon-10 to produce a lactone bridge in almost all of the $C_{19}$-gibberellins.

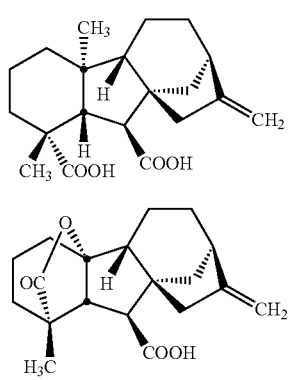

The ent-gibberellane ring system can contain many structural modifications, accounting for the large number of known gibberellins. Naturally occurring gibberellins with identified structures are allocated an "A number" (MacMillan et al. (1968) Nature 217:170-171). At present, 126 naturally occurring gibberellins of plant and fungal origin are known. Current structural information on gibberellins can be found at the website plant-hormones.bbsrc.ac.uk/gibberellin_information2.htm.

Variations in gibberellin structure arise in several ways. Carbon-20 can exist in different oxidative states, for example, methyl (—$CH_3$), hydroxymethyl (—$CH_2OH$), aldehyde (—CHO), or carboxylic acid (—COOH). The ent-gibberellane skeleton especially that of the $C_{19}$-gibberellins, can also contain additional functional groups. Hydroxyl (—OH) groups are frequently inserted into the ring system; insertion of epoxide (>O) and ketone (=O) functions also occurs, although less commonly. The position and/or stereochemistry of substituent groups can affect the biochemical and physiological significance of the molecules. Substituent groups positioned above the ring plane are said to be in the β-configuration; their bonding to the ring is designated by a solid, elongated triangle. Substituent groups positioned below the ring plane are said to be in the α-configuration; their bonding to the ring is designated by a dashed, elongated triangle. The attachment of substituent groups in the plane of the ring system is indicated by a straight line.

Gibberellins can exist as conjugates, for example, with a hexose or pentose molecule such as glucose. An ether or an ester linkage may link such a glucose molecule to the gibberellin. Such conjugation may temporarily or permanently inactivate the activity of a gibberellin within a plant.

The biological activity of different gibberellins varies, and various gibberellins within a plant can be precursors, biosynthetic intermediates, or deactivation products of active gibberellins. Three structural features are commonly associated with gibberellin biological activity: a 3-hydroxyl group, a 7-carboxyl group, and a lactone ring. Broadly speaking, a compound possessing the ent-gibberellane ring system but lacking one or more of these structural features can be considered a gibberellin precursor, an intermediate, or a derivative.

The compositions and methods of the invention generally employ active forms of gibberellic acids, gibberellic acid precursors, gibberellic acid intermediates or gibberellic acid derivatives, for example, those having structures related to formulae IV and V as described above. Gibberellins having such structures can have a variety of substituents including hydroxy (—OH), carboxylate (—COOH), ether (—O), methyl (—$CH_3$), methylene (=$CH_2$), lactone (—CO—O—) ring, hydroxymethylene (—$CH_2$—OH), formyl (CHO), and related substituents in a variety of positions. The gibberellins employed can also have double bonds within the ring structure at different positions.

In some embodiments, the gibberellic acids can have any of formulae VI, VIa, or VIb.

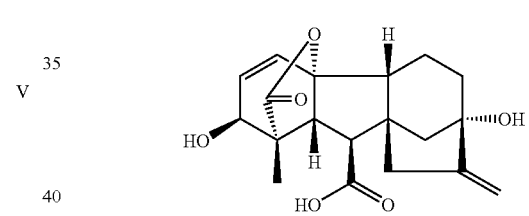

Gibberellin having formula VI is often referred to as Gibberellin $A_3$.

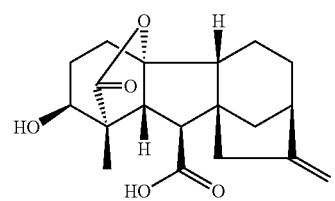

Gibberellin having formula VIa is often referred to as Gibberellin $A_4$.

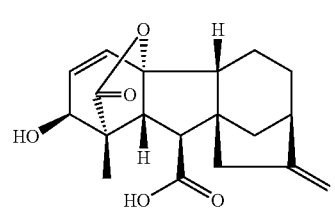

Gibberellin having formula VIb is often referred to as Gibberellin $A_7$.

When present in the compositions of the present invention, gibberellic acids or their derivatives can be used in an amount of about 0.001% to about 50%, or from about 0.01% to about 20%, or from about 0.01% to about 10%, or from about 0.05% to about 5%, or from about 0.05% to about 2% of the composition. According to the invention, in situ concentrations of an active gibberellic acid ranging from about $10^{-4}$ M to about $10^{-6}$ M are effective for increasing epidermal cell proliferation. Compositions having about 0.5% gibberellic acid are shown herein to promote skin turnover.

Jasmonic Acid Compounds

Jasmonic acid compounds employed in the invention include jasmonic acid and jasmonic acid derivatives available to one of skill in the art. Such compounds include jasmonic acid, methyl jasmonate and their isomers. In the present invention jasmonic acid and jasmonic acid derivatives used also include synthetic and natural stereoisomers of jasmonic acid, dihydrojasmonic acid, hydroxy jasmonic acid and dihydro-hydroxy jasmonic acid. Further examples of jasmonic acid derivatives that may be used in the invention include compounds having any one of formulae VII, VIII, IX or X.

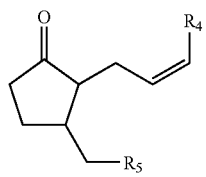

VII wherein:
$R_4$ is alkyl;
$R_5$ is COOR, or —(CH$_2$)n-OX, where n is an integer of from 1 to 20;
R is H, or alkyl; and
X is H, or 1 to 6 sugar residues (e.g., hexoses or pentoses).

In general, the alkyl groups employed in these jasmonic acid compounds have about one to twenty carbon atoms, although in some embodiments lower alkyl groups are used, for example, alkyl groups with about one to eight carbon atoms. Alkyl groups with even lower numbers of carbon atoms can also be used, for example, alkyl groups with one to six, or one to three carbon atoms.

In some embodiments, jasmonic acid is employed in the compositions of the invention. Jasmonic acid is a compound of formula VII wherein $R_4$ is $C_2H_5$ and $R_5$ is COOH.

Another jasmonic acid compound employed in the invention is a compound of formula VIII

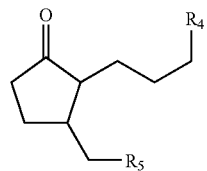

VIII wherein:
$R_4$ is alkyl;
$R_5$ is COOR, or —(CH$_2$)n-OX, where n is an integer of from 1 to 20;
R is H, or alkyl; and
X is H, or 1 to 6 sugar residues (e.g., hexoses or pentoses).

In some embodiments, dihydrojasmonic acid is employed in the compositions of the invention. Dihydrojasmonic acid is a compound of formula VIII wherein $R_4$ is $C_2H_5$ and $R_5$ is COOH.

Another jasmonic acid compound employed in the invention is a compound of formula IX

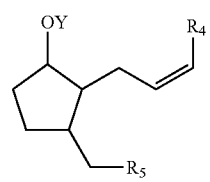

IX wherein:
$R_4$ is alkyl;
$R_5$ is COOR, or —(CH$_2$)n-OX, where n is an integer of from 1 to 20;
R is H, or alkyl;
X is H, or 1 to 6 sugar residues (e.g., hexoses or pentoses); and
Y is H, alkyl, or 1 to 6 sugar residues (e.g., hexoses or pentoses).

In some embodiments, hydroxy jasmonic acid is employed in the compositions of the invention. Hydroxy jasmonic acid is a compound of formula IX wherein $R_4$ is $C_2H_5$ and $R_5$ is COOH.

Another jasmonic acid compound employed in the invention is a compound of formula X.

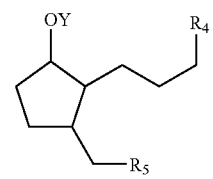

X wherein:
$R_4$ is alkyl;
$R_5$ is COOR, or —(CH$_2$)n-OX, where n is an integer of from 1 to 20;
R is H, or alkyl;
X is H, or 1 to 6 sugar residues (e.g., hexoses or pentoses); and
Y is H, alkyl, or 1 to 6 sugar residues (e.g., hexoses or pentoses).

In some embodiments, dihydro-hydroxyjasmonic acid is employed in the compositions of the invention. Dihydro-hydroxyjasmonic acid is a compound of formula X wherein $R_4$ is $C_2H_5$ and $R_5$ is COOH.

When present in the compositions of the present invention, jasmonic acids or jasmonic acid derivatives can be used in an amount of from about 0.001% to about 50%, or from about 0.01% to about 20%, or from about 0.01% to about 10%, or from about 0.05% to about 5%, or from about 0.05% to about 2% of the composition. According to the invention, in situ concentrations of jasmonic acid ranging from about $10^{-4}$ M to about $10^{-6}$ M are effective for increasing cell proliferation in epidermal tissues. As illustrated herein solutions of about 0.025% jasmonic acid are effective for promoting skin turnover and renewal.

Additional Ingredients

In another embodiment, the compositions and methods of the invention include administering to the female mammal an effective amount of retinoid or carotenoid and/or one or more nucleotide(s) or nucleoside(s). These compositions and methods can increase the expression of $P2Y_2$ receptors or estrogen receptors or vascular endothelial growth factor in vaginal or cervical epithelial cells.

In some embodiments, the compositions of the invention can include one or more retinoids or carotenoids. The IUPAC-IUB Joint Commission on Biochemical Nomenclature states that "retinoids are a class of compounds consisting of four isoprenoid units joined in a head to tail manner." All retinoids may be formally derived from a monocyclic parent compound containing five carbon-carbon double bonds and a functional group at the terminus of the acyclic portion. The basic retinoid structure can be subdivided into three segments, namely the polar terminal end, the conjugated side chain, and the cyclohexenyl ring. The basic structures of the most common natural retinoids are called retinol, retinaldehyde, and retinoic acid. However, retinoids of this invention are not limited to just retinol, retinaldehyde, and retinoic acid. Instead, the retinoids and carotenoids of the invention also include compounds falling within Formula XIA or XIB:

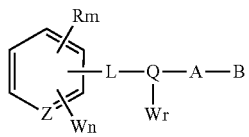

XIA

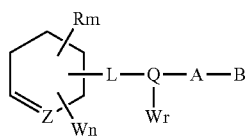

XIB wherein:

Z is CH, or N;

R is H or alkyl of 1 to 6 carbons;

m is an integer having the value of 0-5;

n is an integer having the value of 0-2;

r is an integer having the value 0-2;

L is —(C=Z)—NH— or —NH—(C=Z)— where Z is O or S;

Q is a phenyl, naphthyl, pyridyl, thienyl, furyl, pyridazinyl, pyrimidinyl, pyrazinyl, thiazolyl, oxazolyl, imidazolyl or pyrazolyl, wherein the phenyl, naphthyl pyridyl, thienyl, furyl, pyridazinyl, pyrimidinyl, pyrazinyl, thiazolyl, oxazolyl, imidazolyl or pyrazolyl group can be substituted with one or two $R^1$ groups;

W is F, Br, Cl, I, $C_{1-6}$ alkyl, fluoro-substituted $C_{1-6}$ alkyl, $NO_2$, $N_3$, OH, $OCH_2OCH_3$, $OC_{1-10}$ alkyl, tetrazol, CN, $SO_2C_{1-6}$-alkyl, $SO_2C_{1-6}$-fluoro-substituted alkyl, SO—$C_{1-6}$ alkyl, CO—$C_{1-6}$alkyl, $COOR_8$, phenyl, phenyl itself substituted with a W group other than with phenyl or substituted phenyl, with the proviso that when X is CH and r is 0 then n is not 0 and at least one W group is not alkyl;

A is $(CH_2)_q$ where q is 0-5, lower branched chain alkyl having 3-6 carbons, cycloalkyl having 3-6 carbons, alkenyl having 2-6 carbons and 1 or 2 double bonds, alkynyl having 2-6 carbons and 1 or 2 triple bonds; and B is COOH or a pharmaceutically acceptable salt thereof, $COOR^8$, $CONR^9R^{10}$, $CH_2OH$, $CH_2OR^{11}$, $CH_2OCOR^{11}$, CHO, $CH(OR^{12})_2$, $CHOR^{13}O$, $COR^7$, $CR^7(OR^{12})_2$, $CR^7OR^{13}O$, where $R^7$ is an alkyl, cycloalkyl or alkenyl group containing 1 to 5 carbons, $R^8$ is an alkyl group of 1 to 10 carbons or trimethylsilylalkyl where the alkyl group has 1 to 10 carbons, or a cycloalkyl group of 5 to 10 carbons, or $R^8$ is phenyl or lower alkylphenyl, $R^9$ and $R^{10}$ independently are hydrogen, an alkyl group of 1 to 10 carbons, or a cycloalkyl group of 5-10 carbons, or phenyl or lower alkylphenyl, $R^{11}$ is lower alkyl, cycloalkyl, lower alkyl substituted cycloalkyl, phenyl or lower alkylphenyl, $R^{12}$ is lower alkyl, and $R^{13}$ is divalent alkyl radical of 2-5 carbons.

In some embodiments, the retinoid or carotenoid is a compound defined by Formula XII:

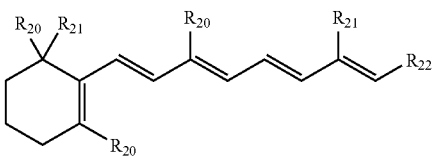

wherein:

$R_{20}$, $R_{21}$ and $R_{22}$ are each independently $C_{1-6}$ alkyl, fluoro-substituted $C_{1-6}$ alkyl, hydroxy-substituted $C_{1-6}$alkyl, $CH_2OH$, $CH_2OR^{11}$, $CH_2OCOR^{11}$, CHO, $CH(OR^{12})_2$, $CHOR^{13}O$, $COR^7$, $CR^7(OR^{12})_2$, or $CR^7OR^{13}O$.

The term alkyl refers to and covers any and all groups that are known as normal alkyl, branched-chain alkyl and cycloalkyl. The term alkenyl refers to and covers normal alkenyl, branch chain alkenyl and cycloalkenyl groups having one or more sites of unsaturation. Similarly, the term alkynyl refers to and covers normal alkynyl, and branch chain alkynyl groups having one or more triple bonds.

Lower alkyl means alkyl groups having 1 to 6 carbons, and 3 to 6 carbons for lower branch chained and cycloalkyl groups. Lower alkenyl is defined similarly having 2 to 6 carbons for normal lower alkenyl groups, and 3 to 6 carbons for branch chained and cyclo-lower alkenyl groups. Lower alkynyl is also defined similarly, having 2 to 6 carbons for normal lower alkynyl groups, and 4 to 6 carbons for branch chained lower alkynyl groups.

Compounds of Formula XIA, XIB and XII can be made as described in U.S. Pat. No. 6,437,129 and U.S. Pat. No. 6,437,003, which are incorporated herein in their entirety.

A pharmaceutically acceptable salt may be prepared for any compounds in this invention having a functionality capable of forming such a salt, for example, an acid or amine functionality. A pharmaceutically acceptable salt is any salt that retains the activity of the parent compound and does not impart any deleterious or untoward effect on the subject to which it is administered and in the context in which it is administered. Pharmaceutically acceptable salts may be derived from organic or inorganic bases. The salt may be a mono or polyvalent ion. Of particular interest are the inorganic ions, sodium, potassium, calcium, and magnesium. Organic salts may by be made with amines, particularly ammonium salts such as mono-, di- and trialkyl amines or ethanolamines. Salts may also be formed with caffeine, tromethamine and similar molecules. Where there is a nitrogen sufficiently basic as to be capable of forming acid addition salts, such may be formed with any inorganic or organic acids or alkylating agent such as methyl iodide. Preferred salts are those formed with inorganic acids such as hydrochloric acid, sulfuric acid or phosphoric acid. Any of a number of simple organic acids such as mono-, di- or tri-acid may also be used.

Some of the compounds of the present invention may have trans and cis isomers. In addition, the compounds of the present invention may contain one or more chiral centers and therefore may exist in enantiomeric and diastereomeric forms. The scope of the present invention is intended to cover all such isomers, as well as mixtures of cis and trans isomers, mixtures of diastereomers and racemic mixtures of enantiomers (optical isomers) as well.

The compositions of the invention can include one or more nucleosides or nucleotides. Such nucleotide or nucleosides can include, for example, dATP, dGTP, dCTP, dTTP, dUTP, ATP, GTP, CTP, TTP, UTP, and any derivative of such nucleotide(s) or nucleoside(s) that is available to one of skill in the art.

In some embodiments, the nucleotide or nucleoside is a compound defined by Formula XIII:

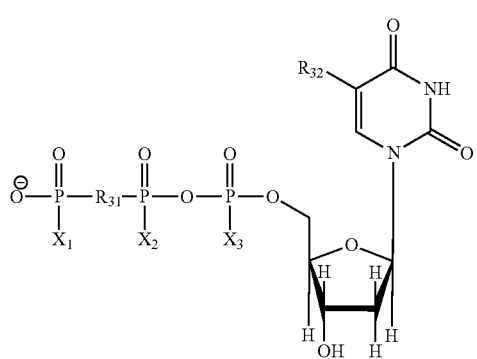

XIII wherein:

$X_1$, $X_2$ and $X_3$ are each independently either $O^-$ or $S^-$. In some embodiments, $X_2$ and $X_3$ are each $O^-$;

$R_{31}$ is O, imido, methylene, or dihalomethylene (e.g., dichloromethylene, difluoromethylene). In some embodiments, $R_{31}$ is oxygen or difluoromethylene.

$R_{32}$ is H or Br. In some embodiments, $R_{32}$ is H. Examples of compounds of Formula XIII are uridine 5'-triphosphate (UTP) and uridine 5'-O-(3-thiotriphosphate) (UTPγS).

In other embodiments, the nucleotide or nucleoside is a compound defined by Formula XIV:

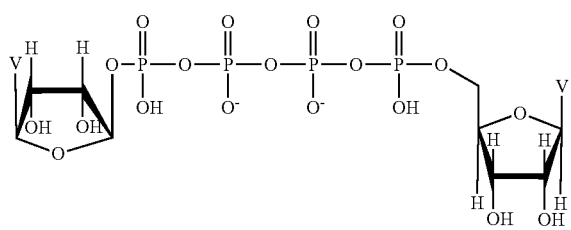

wherein V is uracil or adenine.

In further embodiments of the invention, the nucleotide or nucleoside is a compound defined by Formula XV:

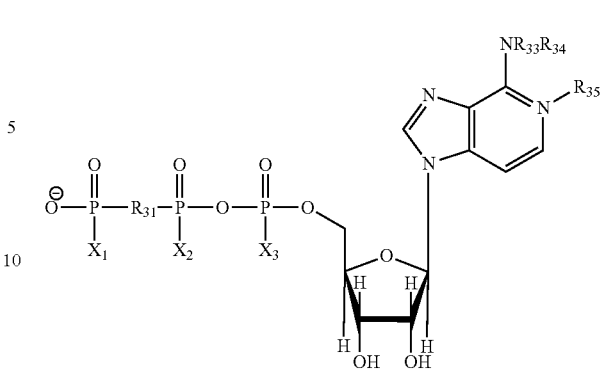

wherein:

$X_1$, $X_2$, $X_3$ and $R_3$, are as defined above;

$R_{33}$ and $R_{34}$ are H when $R_{35}$ is nothing and there is a double bond between N-1 and C-6 (adenine), or $R_{33}$ and $R_{34}$ are H when $R_{35}$ is O and there is a double bond between N-1 and C-6 (adenine 1-oxide), or $R_{33}$, $R_{34}$ and $R_{35}$ taken together are —CH=CH—, forming a ring from N-6 to N-1 with a double bond between N-6 and C-6 (1,$N^6$-ethenoadenine).

In still further embodiments of the invention, the nucleotide or nucleoside is a compound defined by Formula XVI:

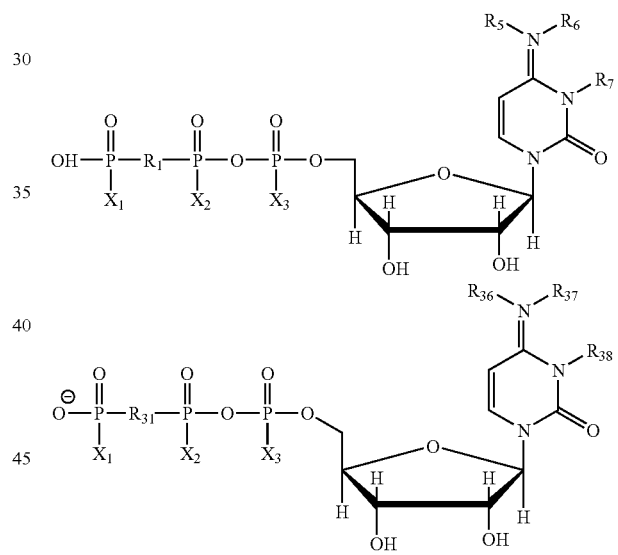

wherein:

$X_1$, $X_2$, $X_3$ and $R_{31}$ are as defined above;

$R_{36}$ and $R_{37}$ are H when $R_{38}$ is nothing and there is a double bond between N-3 and C-4 (cytosine), or, $R_{36}$, $R_{37}$ and $R_{38}$ taken together are —CH=CH—, and form a ring from N-3 to the nitrogen attached to $R_{36}$ and $R_{37}$ (3,$N^4$-ethenocytosine).

Hence, compositions of the invention can contain one or more compounds of Formula XIII, XIV, XV or XVI in an amount effective to stimulate mucous secretions in the vagina or reproductive passages of a female.

Compounds illustrative of the compounds of Formula XIII above include: (a) uridine 5'-triphosphate (UTP); (b) uridine 5'-O-(3-thiotriphosphate) (UTPγS); and (c) 5-bromo-uridine 5'-triphosphate (5-BrUTP). These compounds are known or may be made in accordance with known procedures, or variations thereof which will be apparent to those skilled in the art. See generally N. Cusack and S. Hourani, Annals N.Y. Acad.

Sci. 603, 172-81 (entitled "Biological Actions of Extracellular ATP"). For example, UTP may be made in the manner described in Kenner, et al., J. Chem. Soc. 1954, 2288; or Hall and Khorana, J. Am. Chem. Soc. 76, 5056 (1954). See Merck Index, Monograph No. 9795 (11th Ed. 1989). UTPγS may be made in the manner described in R. S. Goody and F. Eckstein, J. Am. Chem. Soc. 93, 6252 (1971).

Compounds illustrative of the compounds of Formula XIV include $P^1,P^4$-di(adenosine-5') tetraphosphate or $P^1,P^4$-di(uridine-5') tetraphosphate. These compounds can be made in accordance with known procedures, or variations thereof which will be described by: P. Zamecnik, et al., Proc. Natl. Acad. Sci. USA 89, 838-42 (1981); and K. Ng and L. E. Orgel, Nucleic Acids Res. 15 (8), 3572-80 (1987). $P^1$, $P^4$-di(uridine-5') tetraphosphate can be prepared by methods similar to that described in C. Vallejo, et al., Biochem. Biophys. Acta 438, 304-09 (1976).

Compounds illustrative of the compounds of Formula XV above include (a) adenosine 5'-triphosphate (ATP) and (b) 1,$N^6$-ethenoadenosine 5'-triphosphate. Compounds illustrative of the compounds of Formula XIV above include (a) cytidine 5'-triphosphate and (b) 3,$N^4$-ethenocytidine 5'-triphosphate. These compounds can be made in accordance with known procedures, or variations thereof which will be apparent to those skilled in the art. For example, phosphorylation of nucleosides by standard methods such as D. Hoard and D. Ott, J. Am. Chem. Soc. 87, 1785-1788 (1965); M. Yoshikawa, et al., Tetrahedron Lett. 5065-68 (1967) and idem., Bull. Chem. Soc. (Jpn) 42, 3505-08 (1969); J. Moffatt and H. Khorana, J. Am. Chem. Soc. 83, 649-59 (1961); and B. Fischer, et al., J. Med. Chem. 36, 3937-46 (1993) and references therein. Etheno derivatives of cytidine and adenosine are prepared by known methods such as: N. Kotchetkov, et al., Tetrahedron Lett. 1993 (1971); J. Barrio, et al., Biochem. Biophys. Res. Commun. 46, 597 (1972); J. Secrist, et al., Biochemistry 11, 3499 (1972); J. Bierndt, et al., Nucleic Acids Res. 5, 789 (1978); K. Koyasuga-Mikado, et al., Chem. Pharm. Bull. (Tokyo) 28, 932 (1980). Derivatives with alpha, beta and gamma thiophosphorus groups can be derived by the following or by adapting methods of: J. Ludwig and F. Eckstein, J. Org. Chem. 54, 631-35 (1989); F. Eckstein and R. Goody, Biochemistry 15, 1685 (1976); R. Goody and F. Eckstein, J. Am. Chem. Soc. 93, 6252 (1971).

Compounds of Formulas XIII, XV or XVI where $R_1$ is $CCl_2$ and $CF_2$ can be prepared by methods similar to that described in G. Blackburn, et al., J. Chem. Soc. Perkin Trans. 1, 1119-25 (1984). Compounds of Formula I, II, III where $R_1$ is $CH_2$ can be prepared by methods similar to that described in T. Myers, et al., J. Am. Chem. Soc. 85, 3292-95 (1963).

In addition, UTP, ATP, CTP, $P^1P^4$-di(adenosine-5') tetraphosphate, 3,$N^4$-ethenocytidine triphosphate, 1,$N^6$-ethenoadenine 5'-triphosphate, adenosine 1-oxide 5'-triphosphate, ATPγS, ATPβS, ATPαS, $AMPPCH_2$—P, AMPPNHP, $N^4$-ethenocytidine and 1,$N^6$-ethenoadenosine are commercially available, for example, from Sigma Chemical Company, PO Box 14508, St. Louis, Mo. 63178.

Methods of Use

The present invention is directed to a variety of methods of treating or preventing vaginal and/or reproductive problems in a female mammal. These methods involve administering to the female mammal an effective amount of vitamin E and/or a plant hormone such as gibberellic acid or jasmonic acid. In general, administration is topical or intravaginal.

Treatment of, or treating, vaginal and/or reproductive problems in a female mammal is intended to include modulation of mucus levels to enhance or diminish fertility in a female mammal, or to alleviate or diminish vaginal dryness in a female mammal. The treatment therefore can include alleviation or diminishment of more than one vaginal and/or reproductive problem in a female mammal.

In one embodiment, the method increases growth of vaginal or cervical epidermal cells. In another embodiment, the method involves increasing the expression of mucin genes, for example, mucin-1, mucin-2, mucin-3A, mucin-3B, mucin-4, mucin-5B, mucin-5AC, mucin-6, mucin-7, mucin-11, mucin-13, mucin-15, mucin-17, mucin-19, mucin-20 and similar mucin genes. Such methods can prevent or treat vaginal dryness in a mammal, or maintain or enhance the normal protective function of vaginal mucus in a mammal.

The term "mammal," as used herein, refers to an animal, in general, a warm-blooded animal. Mammals include cattle, buffalo, sheep, goats, pigs, horses, dogs, cats, rats, rabbits, mice, and humans. Also included are other livestock, domesticated animals and captive animals.

Treatment involves administering an effective amount of vitamin E and/or a plant hormone. The vitamin E, gibberellic acid and/or jasmonic acid may be administered as a composition that contains other ingredients, for example, one or more nucleotide(s) or nucleoside(s), other vitamins (e.g., a retinoid or carotenoid such as vitamin A), aloe vera and the like. In general, compositions containing vitamin E, gibberellic acid or jasmonic acid with or without other compound(s) are administered intravaginally.

Compositions

The compositions of the invention are administered to improve the health of the female reproductive system, to stimulate secretion of lubricating fluids (mucus), promote cell growth, treat regression of vaginal mucosa and rejuvenate the female reproductive system.

To achieve the desired effect(s), the composition may be administered as single or divided dosages, for example, of at least about 0.001 μg/kg to about 100 to 200 mg/kg, of about 0.01 μg/kg to about 30 to 50 mg/kg, about 0.1 μg/kg to about 10 to 20 mg/kg or about 1.0 μg/kg to about 1.0 to about 10 mg/kg of body weight of one or more retinoid or carotenoid or nucleotide or nucleoside, although other dosages may provide beneficial results. The amount administered will vary depending on various factors including, but not limited to, the disease, the weight, the physical condition, the health, the age of the mammal, and whether prevention of reproduction or treatment of vaginal dryness is to be achieved. Such factors can be readily determined by the clinician employing animal models or other test systems that are available in the art.

Administration of the therapeutic agents in accordance with the present invention may be in a single dose, in multiple doses, in a continuous or intermittent manner, depending, for example, upon the recipient's physiological condition, whether the purpose of the administration is therapeutic or prophylactic, and other factors known to skilled practitioners. The administration of the compositions of the invention may be essentially continuous over a pre-selected period of time or may be in a series of spaced doses. Local administration is generally contemplated.

The compositions are prepared by combining the active ingredients in the appropriate concentrations. Other active or inactive agents selected by one of skill in the art can optionally be added. The absolute weight of a given active agent included in a unit dose can vary widely. For example, about 0.001 μg to about 50 mg, or about 0.01 μg to about 10 mg, or about 0.1 μg to about 1 mg, of at least one vitamin E, gibberellic acid or jasmonic acid, or of a plurality of vitamin E compounds or gibberellic acid compounds or jasmonic acid compounds can be administered. Alternatively, the unit dosage can vary from about 0.001 μg to about 1000 μg, from about 0.01 µg to about 750 µg, from about 0.1 µg to about 1 mg, from about 1.0 µg to about 750 µg, from about 2.5 µg to about 600 µg, from about 5.0 µg to about 500 µg, or from about 7.5 µg to about 400 µg.

Daily doses of the compositions of the invention can vary as well. Such daily doses can range, for example, from about 0.001 mg/day to about 50 mg/day, from about 0.01 mg/day to about 25 mg/day, from about 0.1 mg/day to about 12 mg/day, from about 0.1 mg/day to about 8 mg/day, from about 0.1 mg/day to about 4 mg/day, and from about 0.1 mg/day to about 2 mg/day of one or more vitamin E, gibberellic acid or jasmonic acid compounds.

The concentration of vitamin E, gibberellic acid or jasmonic acid within a composition can also vary. For example, the concentration can vary from about 0.1 µM to about 1000 µM, or from about 0.5 µM to about 500 µM, or from about 1 µM to about 300 µM, or from about 5 µM to about 200 µM, or from about 10 µM to about 100 µM.

Thus, one or more suitable unit dosage forms comprising the therapeutic compositions of the invention can be administered by a variety of routes including oral, parenteral (including subcutaneous, intravenous, intramuscular and intraperitoneal), rectal, dermal, transdermal, intrathoracic, intrapulmonary intravaginal and intranasal (respiratory) routes. The therapeutic compositions may also be formulated for sustained release (for example, using microencapsulation, see WO 94/07529, and U.S. Pat. No. 4,962,091). The formulations may, where appropriate, be conveniently presented in discrete unit dosage forms and may be prepared by any of the methods well known to the pharmaceutical arts. Such methods may include the step of mixing the therapeutic agent with liquid carriers, solid matrices, semi-solid carriers, finely divided solid carriers or combinations thereof, and then, if necessary, introducing or shaping the product into the desired delivery system.

When the therapeutic compositions of the invention are prepared for intravaginal administration, they are generally combined with a pharmaceutically acceptable carrier, diluent or excipient to form a pharmaceutical formulation, or unit dosage form. For intravaginal administration, the compositions may be present as a solution, a suspension, an emulsion, a powder, a granular formulation, or in a natural or synthetic polymer or resin. The active compositions may also be presented as a bolus or paste. Intra vaginally administered therapeutic compositions of the invention can also be formulated for sustained release, e.g., the compositions can be coated, micro-encapsulated, or otherwise placed within a sustained delivery device. The total active ingredients in such formulations comprise from 0.1 to 99.9% by weight of the formulation.

By "pharmaceutically acceptable" it is meant a carrier, diluent, excipient, and/or salt that is compatible with the other ingredients of the formulation, and not deleterious to the recipient thereof.

Pharmaceutical formulations containing the therapeutic compositions of the invention can be prepared by procedures known in the art using well-known and readily available ingredients. For example, the composition can be formulated with common excipients, diluents, or carriers, and formed into tablets, capsules, solutions, suspensions, powders, aerosols and the like. Examples of excipients, diluents, and carriers that are suitable for such formulations include buffers, as well as fillers and extenders such as starch, cellulose, sugars, mannitol, and silicic derivatives. Binding agents can also be included such as carboxymethyl cellulose, hydroxymethylcellulose, hydroxypropyl methylcellulose and other cellulose derivatives, alginates, gelatin, and polyvinylpyrrolidone. Moisturizing agents can be included such as glycerol, disintegrating agents such as calcium carbonate and sodium bicarbonate. Agents for retarding dissolution can also be included such as paraffin. Resorption accelerators such as quaternary ammonium compounds can also be included. Surface active agents such as cetyl alcohol and glycerol monostearate can be included. Adsorptive carriers such as kaolin and bentonite can be added. Lubricants such as talc, calcium and magnesium stearate, and solid polyethyl glycols can also be included. Preservatives may also be added. The compositions of the invention can also contain thickening agents such as cellulose and/or cellulose derivatives. They may also contain gums such as xanthan, guar or carbo gum or gum arabic, or alternatively polyethylene glycols, bentones and montmorillonites, and the like. The compositions of the invention can also contain other vitamins such as vitamin A, vitamin B, vitamin C or vitamin D. In one embodiment, the compositions of the invention can also contain aloe vera.

The therapeutic compositions of the invention can also be formulated as emulsions, suspensions, aqueous or anhydrous solutions or dispersions, or alternatively the form of an emulsion or suspension or salve for convenient intravaginal administration. The active compositions and other ingredients may form suspensions, solutions, or emulsions in oily or aqueous vehicles, and may contain formulatory agents such as suspending, stabilizing and/or dispersing agents. Alternatively, the active compositions and other ingredients may be in powder form, obtained by aseptic isolation of sterile solid or by lyophilization from solution, for constitution with a suitable vehicle, e.g., sterile, pyrogen-free water, before use.

These formulations can contain pharmaceutically acceptable carriers, vehicles and adjuvants that are well known in the art. It is possible, for example, to prepare solutions using one or more organic solvent(s) that is/are acceptable from the physiological standpoint, chosen, in addition to water, from solvents such as acetone, ethanol, isopropyl alcohol, glycol ethers such as the products sold under the name "Dowanol," polyglycols and polyethylene glycols, $C_1$-$C_4$ alkyl esters of short-chain acids, ethyl or isopropyl lactate, fatty acid triglycerides such as the products marketed under the name "Miglyol," isopropyl myristate, animal, mineral and vegetable oils and polysiloxanes.

It is possible to add, if necessary, an adjuvant chosen from antioxidants, surfactants, other preservatives, film-forming, keratolytic or comedolytic agents, perfumes, flavorings and colorings. Antioxidants such as t-butylhydroquinone, butylated hydroxyanisole, butylated hydroxytoluene and α-tocopherol and its derivatives can be added.

Additionally, the compositions are well suited to formulation as sustained release dosage forms and the like. The formulations can be so constituted that they release the active composition within the female reproductive system over a period of time. Coatings, envelopes, and protective matrices may be made, for example, from polymeric substances, such as polylactide-glycolates, liposomes, microemulsions, microparticles, nanoparticles, or waxes.

For intravaginal administration, the therapeutic agents may be formulated as is known in the art for direct application to the vaginal area. Forms chiefly conditioned for vaginal application take the form, for example, of creams, milks, gels, dispersion or microemulsions, lotions thickened to a greater or lesser extent, impregnated pads, ointments, aerosol formulations (e.g., sprays or foams), creams, lotions, pastes, jellies, sprays, and aerosols. Alternatively, the composition can be formulated to be part of an adhesive polymer, such as polyacrylate or acrylate/vinyl acetate copolymer.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. Liquid sprays are conveniently delivered from pressurized packs, for example, via a specially shaped closure. The active compositions can also be delivered via iontophoresis, e.g., as disclosed in U.S. Pat. No. 4,140,122; 4,383,529; or 4,051,842. The percent by weight of a therapeutic agent of the invention present in a vaginal formulation will depend on various factors, but generally will be from 0.01% to 95% of the total weight of the formulation, and typically 0.1-85% by weight.

The pharmaceutical formulations of the present invention may include, as optional ingredients, pharmaceutically acceptable carriers, diluents, solubilizing or emulsifying agents, and salts of the type that are available in the art. Examples of such substances include normal saline solutions such as physiologically buffered saline solutions and water. Specific non-limiting examples of the carriers and/or diluents that are useful in the pharmaceutical formulations of the present invention include water and physiologically acceptable buffered saline solutions such as phosphate buffered saline solutions with a pH of about 4.5 to about 5.5.

Furthermore, the active ingredients may also be used in combination with other therapeutic agents, for example, anti-microbial agents, pain relievers, anti-inflammatory agents, vitamins (e.g., vitamin A, B, C or D), aloe vera and the like, whether for the conditions described or some other condition.

The present invention further pertains to a packaged pharmaceutical composition for controlling reproduction and/or vaginal dryness such as a kit or other container. The kit or container holds a therapeutically effective amount of a pharmaceutical composition for controlling reproduction and/or vaginal dryness and instructions for using the pharmaceutical composition for control of reproduction and/or vaginal dryness. The pharmaceutical composition includes a composition of the present invention, in a therapeutically effective amount such that vaginal dryness is controlled.

In addition, the invention provides a vaginal insert that can release the vitamin E, gibberellic acid or jasmonic acid in a controlled fashion. Such a vaginal insert can be biodegradable or non-biodegradable. The vaginal insert provides sustained release of the active ingredients at an appropriate rate for achieving the desired level of mucus secretion, gene expression and cellular proliferation.

In some embodiments, the active ingredients can be formulated with oleaginous bases or ointments to form the vaginal insert. This class of formulations comprises the active ingredients and hydrocarbon-based semisolids containing dissolved and/or suspended bacteriostats/preservatives and a buffer system. The petrolatum component in these bases can be any paraffin ranging in viscosity from mineral oil employing incorporated isobutylene, colloidal silica, or stearate salts to paraffin waxes. White and yellow petrolatum are examples of such systems. Bases of this class can be made by incorporating high-melting waxes into a fluid mineral oil via fusion or by incorporation of polyethylene into mineral oil at elevated temperature. Polysiloxanes (also known as silicones) are suitable for use in these bases and typically have a viscosity in the range of about 0.5 to 10.sup.6 centistokes. The organic entities attached to the polysiloxane are preferably lower molecular weight hydrocarbon moieties having from 1 to 8 carbons each, such as lower alkyl, lower alkenyl, phenyl and alkyl substituted phenyl, and phenyl(lower)alkyl, such as benzyl.

In such a moiety, each lower alkyl or alkenyl group preferably has 1 to 3 carbons inclusive, such as in a dimethylsiloxane polymer.

Absorption bases can used with such an oleaginous system. In addition to the active ingredients, additional ingredients with the capacity to emulsify a significant quantity of water are employed. Water-in-oil (w/o) emulsions can be formed wherein the external phase is oleaginous in character. Preservatives/bacteriostats, such as the parabens, buffer systems, etc. can be incorporated into these bases as emulsified aqueous solutions together with the active ingredient. Diverse additives are conveniently used as the emulsifier, and these include, but are not limited to, cholesterol, lanolin (which contains cholesterol and cholesterol esters and other emulsifiers), lanolin derivatives, beeswax, fatty alcohols, wool wax alcohols, low HLB (hydrophobe/lipophobe balance) emulsifiers, and assorted ionic and nonionic surfactants, singularly or in combination.

Water-In-Oil (W/O) emulsion bases can be employed in the vaginal inserts of the invention. These formulations can be an expansion of the general class of absorption bases that includes liquids or creams. They can be prepared by taking a mixture of the active ingredients with oil phase ingredients, bacteriostats/preservatives and buffer salts which are dissolved or suspended therein and to which water has been added to form a water-in-oil emulsion.

Oil-In-Water (O/W) emulsion bases can also be utilized in the vaginal inserts of the invention. These systems are semi-solid emulsions, microemulsions, or foam emulsion systems containing metronidazole. Usually such a system has a "creamy white" appearance. Typically, the internal oil phase is in the range in percentage composition of about 10% to about 40% oil by weight and the external phase may contain 80% or more water. The oleaginous phase may contain, but is not limited to, long-chain alcohols (cetyl, stearyl), long-chain esters (myristates, palmitates, stearates), long-chain acids (palmitic, stearic), vegetable and animal oils and assorted waxes. These can be made with anionic, cationic, nonionic or amphoteric surfactants, or with combinations especially of the nonionic surfactants. The examples below are exemplary of these systems, but those skilled in the art will appreciate that substitutions and additions or omissions of the specified components could be made by one who is skilled in the art.

Vaginal inserts and suppositories containing the active ingredients can be, for example, oleaginous in nature that melt at body temperature, or polyethylene glycol-based compositions that dissolve in the vaginal fluids. Additional bases for suppositories are glycerin and glycerinated gelatin.

The active ingredients can also be formulated into vaginal inserts using buffered gels made with gelling agents. Some examples of these gelling agents are: cellulosics, cationic polymers, polyoxyalkylenes, and carboxyvinyl polymers. Cellulosics useful in the formulations of the invention include, for example, methyl cellulose, carboxymethyl cellulose, hydroxyethyl cellulose, and hydroxypropyl cellulose. Cationic Polymers useful in the formulations of the invention include "Polyquaternium-10", a polymeric quaternary ammonium salt of hydroxyethyl cellulose reacted with a trimethyl ammonium-substituted epoxide, and the like. Polyoxyalkylenes useful in the invention include olyoxyethylene-polyoxypropylene esters of lanolin and derivatives thereof. Carboxyvinyl polymers useful for the formulations of the invention include cross-linked acrylic acid polymers, e.g., those commercially available from B.F. Goodrich Co., Akron, Ohio, under the designation CARBOPOL™.

The vaginal insert can comprise a mixture or coating of polymers that provide release of the active agents at a constant rate over a prolonged period of time. In some embodiments, the vaginal insert comprises water-soluble pore forming agents, such as polyethylene glycol (PEG) that can be mixed with water insoluble polymers to increase the durability of the insert and to prolong the release of the active ingredients. Such a water-soluble pore forming agent can be polyethylene glycol, polypropylene glycol, a mixture or polymer of sugars (lactose, sucrose, dextrose, etc.), salts, poloxamers, polyvinyl alcohol and other water soluble food grade and other excipients.

When PEG is used as a pore forming agent, the molecular weight of PEG is in the range from about 200 to about 20,000, alternatively, from about 400 to about 8,000. For example, PEG having a molecular weight of about 540 to about 8,000 is used. In another embodiment, the PEG has a molecular weight of about or above 1,000 to about 8,000. The molecular weight of PEG used for the coating with the formulation of the invention will depend on the ability of PEG to form a coating film that is non-sticky, having enough strength and creating adequate pore size for controlling the release of active ingredients over the desired time period both in vitro and in vivo.

The pore-forming agent is used in the formulation of the invention in the amount effective to regulate the release of a biologically active compound at a desired rate. Preferably, the effective amount of the pore-forming agent provides long term delivery of the active agent thus increasing the useful life of a sustained-release drug implant. The effective amount of the pore forming agent will depend on the desired rate and duration of the release and the ability to form a continuous microporous film during the coating process. To enable release duration over longer periods of time PEG with higher molecular weights is used. For example, PEG 8000 can provide release over a period of time that is longer than 100 days, when used in a concentration from 10 to 50%, preferably from 20 to 45% and most preferably from 30 to 45%. The concentration of PEG is expressed herein in % weight per dry basis and represents the concentration of PEG in the coating film after drying. Similarly, the thickness of the coating film is from 5 to 50 μm, preferably 30 from 10 to 30 μm and most preferably from 15 to 25 μm.

A good correlation exists between the dissolution rate of active agents and the amount of pore forming agent incorporated in the coating film based on in vitro and in vivo studies shown in the Examples. Depending on the desired length of release, the PEG concentration ranges can be adjusted as needed. For example, in vivo duration of a coated insert may be predicted simply from the in vitro dissolution rate of the active agent at the 120-hour time point.

The vaginal insert of the invention may also comprise a water insoluble polymer. Examples of such polymers are ethylcellulose, acrylic resins, co-polymer of methacrylic acid and acrylic acid ethyl ester, polylactic acid, PLGA, polyurethane, polyethylene vinyl acetate copolymer, polystyrene-butadiene copolymer and silicone rubber, or mixtures thereof. For example, polymers sold under trade names Aquacoat ECD 30 and Eudragit RS 30 and NE 30D (registered trademarks of Rhom Tech, Inc.) can be used.

A polymer suitable for use in this invention is a polymer that is capable of forming a continuous coating film during the process of spraying and drying with a pore-forming agent. The rate controlling film prepared with such a polymer is very stable during implantation. The film should have enough strength to withstand tear and inner osmotic pressure, and have the stability not to swell or hydrate during the implantation life.

In one embodiment, the coating formulation of the invention is used to coat pellets comprising the active ingredients that are compressed to form a solid, biodegradable insert and then administered for stimulating mucus secretion, gene expression and/or cellular proliferation.

The invention is further illustrated by the following non-limiting Examples.

Example 1

Vitamin E Increases Vaginal Cell Growth and Mucus Secretion

This Example shows that vitamin E can enhance human cervical epithelial cell growth and increase the expression of mucin-4 in an atrophic vaginitis model.

Materials and Methods

Cell Culture. Human cervical epithelial cells (ME-180, ATCC) were propagated in culture at 37° C. using 5% $CO_2$ in McCoy's 5A media (Invitrogen) with 10% heat-inactivated fetal bovine serum (Invitrogen). Vitamin E was purchased from ICN Biomedicals. Vitamin E stock solutions were made up in absolute ethanol.

RNA Extraction from ME-180 cells. ME-180 cells were plated at $2 \times 10^5$ cells per T75 flask (15 mL total volume) and were allowed to propagate for four days. On day four, the media was removed. Fifteen mL of McCoy's 5A media with or without 10% FBS containing 0 or 1 μM vitamin E were added to ME-180 cells in duplicate. ME-180 cells were incubated with these solutions for 24 hours. The media was removed, and 1500 μL of lysis buffer was added to the flasks. The cells were scraped off of the flask with a cell scraper. The RNA was isolated using the Ambion RNAqueous kit according to the manufacturer's instructions. Precipitated RNA was resuspended in DEPC-treated water with 1 μL of RNase inhibitor.

Reverse Transcription of RNA. Approximately 7 μL of RNA was incubated with 3 μL of primer at 80° C. for 10 minutes then immediately placed on ice. A master mix containing 4 μL DEPC water, 4 μL 5× reaction buffer, 1 μL dNTPs, 1 μL of RNase inhibitor, and 1 μL of reverse transcriptase was made for the reactions. Ten μL of master mix was added to the RNA/primer solution and placed at 42° C. for 2 hours. The resulting cDNA was incubated with 3.5 μL of NaOH solution at 70° C. for 10 minutes to hydrolyze the remaining RNA. Five μL of 0.5M Tris/EDTA was added to neutralize the solution. To precipitate the cDNA, 125 μL of 3M $NH_4OAc$, 5 μL of linear polyacrylamide, and 700 μL of absolute ethanol were added. The solutions were vortexed and placed at −20° C. overnight. Samples were centrifuged at 14000 rpm at 4° C. for 30 minutes. The ethanol was removed, and the samples were allowed to dry for 10 minutes. The cDNA was resuspended in 10-12 μL of PCR grade water.

Polymerase Chain Reaction (PCR). A master mix using the Advantage 2 PCR kit (Ambion) was made for the PCR reactions containing 37-38 μL of PCR grade water, 5 μL of 10×PCR buffer, 1 μL of dNTPs, 1 μL of β-actin primers (10 μM, optional control), and 2 μL of test primers (10 μM, $P2Y_2$, or Mucin-4 (MUC-4)). Two microliters of cDNA and 1 mL of DNA polymerase were added. Cycling conditions were as follows: 5 min at 95° C.; 25-30 cycles (30 sec at 95° C., 1 min at 65° C., 3 min at 68° C.); 5 min at 68° C.

The PCR primers employed were as follows:

```
P2Y₂-specific primers
(yielding a PCR product of 650 bp):
                                   (SEQ ID NO: 1)
coding strand: 5'-TGTCTTCGCCCTCTGCTTCC-3'
```

-continued

```
                                          (SEQ ID NO: 2)
noncoding strand: 5'-GTCAGGCCAGGGGTGTCATT-3'

β-actin-specific primers (PCR product 300 bp):
                                          (SEQ ID NO: 3)
coding strand: 5'-AGTCGGTTGGAGCGAGCATC-3'
                                          (SEQ ID NO: 4)
noncoding strand: 5'-GGGCACGAAGGCTCATCATT-3'

Mucin-4 (MUC-4) specific primers
(PCR product 800 bp):
                                          (SEQ ID NO: 5)
coding strand:5'-AGCCCAGGACTGTGGTCTGC-3'
                                          (SEQ ID NO:6)
noncoding strand: 5'-GCTCACGTTCAGGGCTGTCA-3'
```

Results

ME-180 cells were incubated with vitamin E at various concentrations for three days. At 10 µM vitamin E, ME-180 cell growth was inhibited (data not shown). However, this may be due to the presence of a larger concentration of ethanol (used as a solvent for vitamin E) in the media. The negative control with the same amount of ethanol (no vitamin E) also showed no ME-180 cell growth. At 1 µM vitamin E, ME-180 cell growth was enhanced more than the corresponding negative control. At 100 nM vitamin E, cell growth was not effected in comparison to the negative control. Therefore, a concentration of 1 µM vitamin E was used to measure changes in RNA expression over a 24 hour period.

ME-180 cells were treated with 0 or 1 µM vitamin E in the presence and absence of fetal bovine serum. Previous results by the inventors had shown that few changes in RNA expression occur in the presence of serum. However, when the serum was removed, ME-180 cell growth slowed down, an effect that is observed in vaginal atrophy. Therefore, ME-180 cells maintained without serum was used as a model of atrophic vaginitis.

After treatment with vitamin E for 24 hours, RNA was isolated from the ME-180 cells. Using reverse transcription, the RNA was converted to cDNA that was then used as template in PCR reactions. In the presence of serum, no significant changes in expression of P2Y2 or mucin-4 were observed, as had been expected (data not shown).

After 24 hour treatment with vitamin E in the absence of serum, mucin-4 expression in ME-180 cells was significantly increased (FIG. 1). Treatment with vitamin E for 24 hours in the absence of serum led to no observable difference in P2Y2 expression, DTR expression, or VEGF expression at the 24 time point (data not shown). However, previous experiments with vitamin A had indicated that after approximately 24 hours in the absence of serum, ME-180 cells begin to express P2Y2. Therefore, it is possible that changes occurred during or after the 24 hour incubation period that were not detected in this experiment.

These data indicate that vitamin E can enhance human cervical epithelial cell growth as well as increase the expression of mucin-4 in an atrophic vaginitis model. Therefore, vitamin E may be useful in the treatment of atrophic vaginitis.

Example 2

Vitamin A Effects Cervical Cell Growth and Gene Expression

The interaction of ME-180 cervical cells with several concentrations of vitamin A derivatives were studied to determine if the vitamin A derivatives would affect ME-180 cellular growth and gene expression.

Figure 2A:
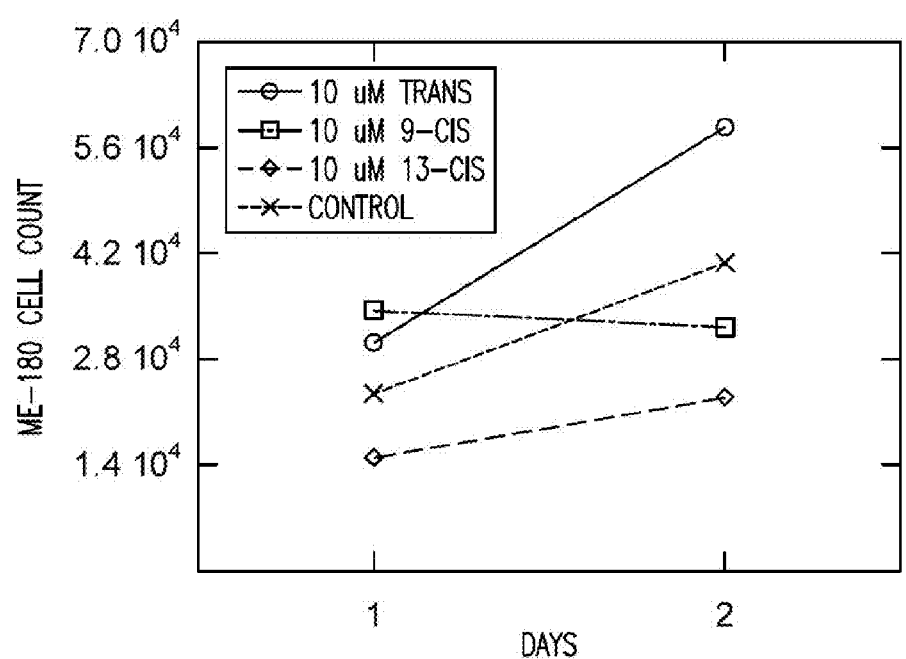
FIG. 2A-2C illustrates the effects of three concentrations of trans-retinoic acid (circles), 9-cis-retinoic acid (square symbols), and 13-cis-retinoic acid (diamonds) on ME-180 cell growth over a period of two days. As a negative control, the effect of media without retinoic acid (crosses) on cell growth is also illustrated.
Figure 2B:
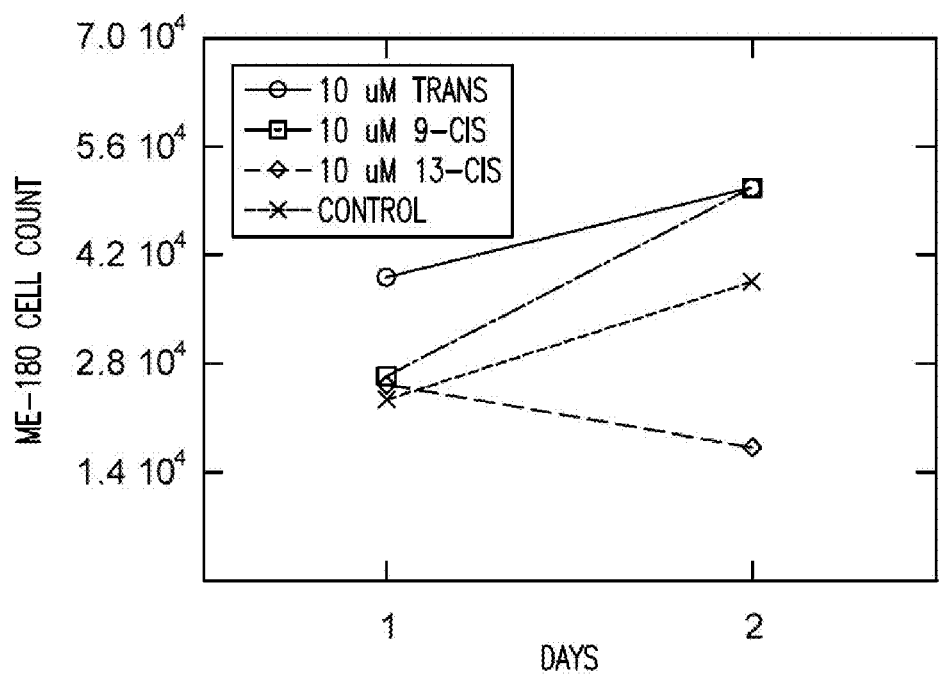
Figure 2C:
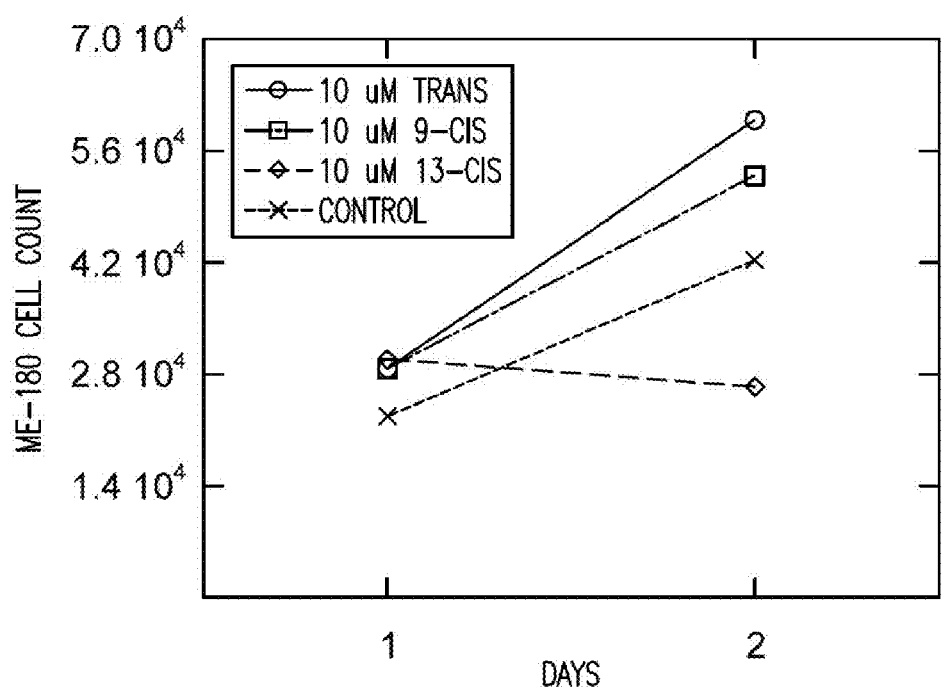
Figure 3:
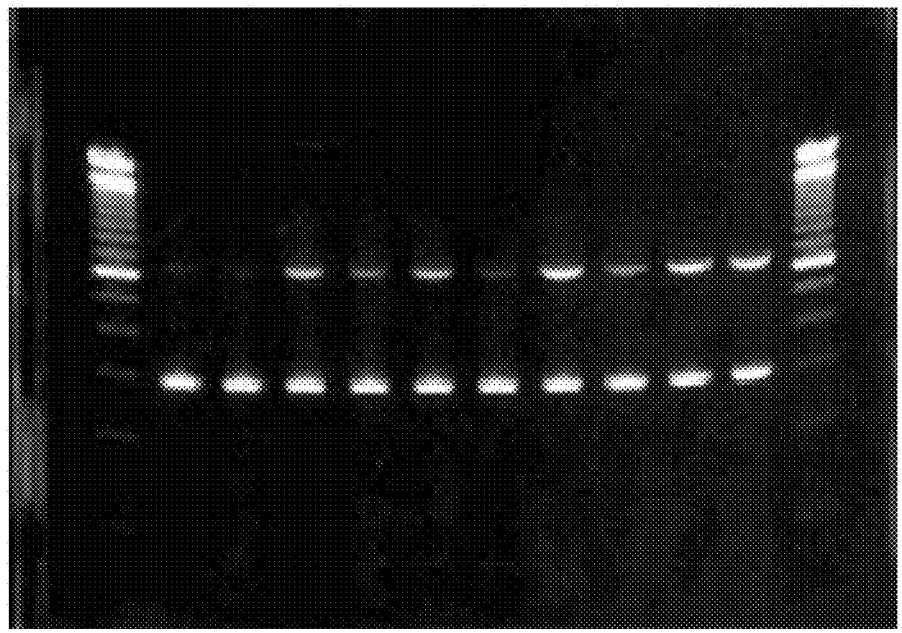
FIG. 3 provides a copy of photograph of an ethidium bromide-stained 2% agarose gel of PCR products using cDNA derived from ME-180 cervical epithelial cell mRNA as template. Two sets of primers were used to generate the products in lanes 2-11: $P2Y_2$-specific primers (top band, 650 bp, lanes 2-11) and β-actin-specific primers (bottom band, 300 bp). Lanes 1 and 12 are DNA size markers. The $P2Y_2$ product can barely be seen in lanes 2, 3, and 7 where the template cDNA was from cervical cells (lane 2), ME-180 cells without vitamin A (lane 3), and ME-180 cells without vitamin A or serum (lane 7), respectively. The addition of 100 nM vitamin A to ME-180 cells caused an increase in $P2Y_2$ expression in the presence of serum (lanes 4-6) and in the absence of serum (lanes 8-11).

Cell Proliferation of ME-180 Cells. ME-180 cells were incubated with vitamin A derivatives for a period of up to 3 days. ME-180 cells were counted on each day. The results of these experiments are shown in FIGS. 2 and 3.

When very low concentrations of vitamin A were used little effect on cell growth was observed. For example, concentrations of 0.0 nM (negative control), 1 nM, 10 nM, and 100 nM trans-retinoic acid, 9-cis-retinoic acid or 13-cis-retinoic acid had little effect on cell growth. However, cells exposed to trans-retinoic acid appeared to be growing slightly faster than cells exposed to other agents or to no agents (unexposed, negative control cells).

Therefore, another experiment using retinoic acid concentrations ranging from 100 nM to 10 µM was performed. As illustrated in FIG. 2, more cells were present after treatment with 1 µM or 10 µM trans-retinoic acid than after treatment with no retinoic acid (negative control). These data indicate that trans-retinoic acid enhances ME-180 cell growth in culture. In contrast, cells treated with 13-cis-retinoic acid did not grow as well as the negative control, indicating that 13-cis-retinoic acid is toxic to ME-180 cells at micromolar concentrations.

Expression Assay Using Polymerase Chain Reaction and ME-180 cDNA. RNA was isolated from ME-180 cells that had been treated with 1 µM or 10 nM trans-retinoic acid (vitamin A) for 24 hours. After precipitation, the RNA was used as a template for DNA synthesis by reverse transcription as described above. PCR techniques were then used to amplify the newly synthesized DNA to determine the approximate level of transcription of the $P2Y_2$ receptor gene (an approximate 600 bp PCR product). "House-keeping genes" or genes that remain at a constant expression level were also amplified by PCR for comparison. The housekeeping genes tested with $P2Y_2$ was β-actin (~300 bp product).

As shown in FIG. 3, addition of control β-actin primers leads to synthesis of an approximate 300 bp cDNA product that is present in approximately equal amounts in all samples. This result indicates that approximately the same amounts of template RNA were present in all samples. However, as is also illustrated in FIG. 3, the $P2Y_2$ product can barely be seen in lanes 2, 3, and 7 where the PCR template was cervical cDNA control, ME-180 cells without vitamin A, and ME-180 cells without vitamin A or serum, respectively. Thus, in the absence of vitamin A, little $P2Y_2$ mRNA is present in ME-180 cells.

However, upon addition of 100 nM vitamin A to ME-180 cells, an increase in $P2Y_2$ expression is observed both in the presence of serum (FIG. 3, lanes 4-6) and in the absence of serum (FIG. 3, lanes 8-11) in the media. These data indicate that low concentrations of vitamin A may be useful in the treatment of atrophic vaginitis.

Figure 4:
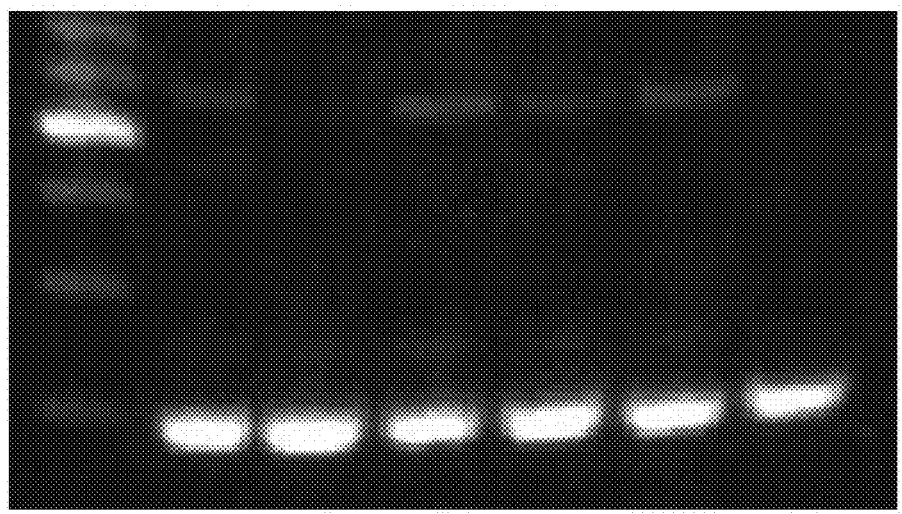
FIG. 4 provides a copy of a photograph of an ethidium bromide-stained 2% agarose gel of PCR products using cDNA derived from ME-180 cervical epithelial cells as template. Lane 1 provides DNA size markers. Two sets of primers were used to generate the PCR products in lanes 2-10: ER-α-specific primers (upper band) and β-actin-specific primers (lower band). In Lane 2 the template was cDNA from ME-180 cells cultured in the presence of serum. In Lanes 3 and 7, the template was cDNA from ME-180 cells cultured in the absence of serum. In Lanes 4-6, the templates were cDNAs from ME-180 cells cultured without serum and treated with 100 nM vitamin A for 4, 8 and 16 hours, respectively. Addition of 100 nM vitamin A to ME-180 cells caused an increase in ER-α expression.

Cell samples exposed to vitamin A in the absence of serum were also tested for expression of other genes that may also affect atrophic vaginitis. Using primers designed to amplify the estrogen receptor alpha (ER-α) gene, PCR was performed using the RNA samples from cells starved of serum. The ER-α product (650 bp) was visible in the control (FIG. 4, lane 2), where the template was cDNA from ME-180 cells cultured in the presence of serum. In samples that did not contain serum or vitamin A, the cDNA fragment signifying ER-α gene expression was not detected (lanes 3 and 7, FIG. 4). However, in the samples that were exposed to 100 nM vitamin A but no serum for 4, 8, and 16 hours, the $ER_2$-α gene was expressed (Lanes 4-6, respectively). These data indicate that vitamin A can induce the expression of $ER_2$-α in cervical epithelial cells cultured in the absence of serum. Increasing the amount of estrogen receptors on epithelial cells in the genital tract may increase the probability that a receptor will be activated by estrogen.

Figure 5:
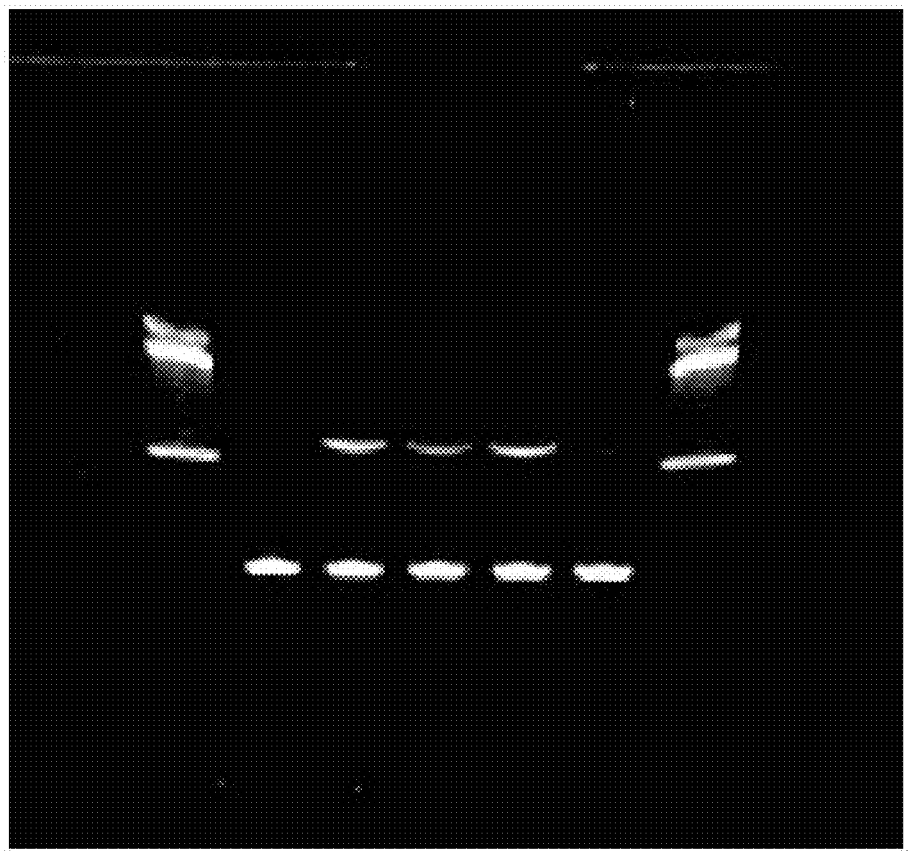
FIG. 5 provides a copy of a photograph of an ethidium bromide-stained 2% agarose gel of PCR products using RNA from various cell types as template. Lanes 1 and 7 provide DNA size markers. Two sets of primers were used to generate the PCR products in lanes 2-6: vascular endothelial growth factor (VEGF) specific primers (upper band) and β-actin-specific primers (lower band). Lanes 2 and 6 provide the PCR products from cDNA derived from untreated ME-180 cells. Lanes 3-5 provide the PCR products from cDNA derived from ME-180 cells treated with 100 nM vitamin A for 4, 8, and 16 hours, respectively.

Moreover, treatment of ME-180 cells with 100 nM vitamin A also increased the expression of vascular endothelial growth factor (VEGF), an important factor involved in blood vessel formation. As illustrated in FIG. 5, an approximate 700 bp product characteristic of VEGF is detected in ME-180 cells treated with 100 nM vitamin A.

These experiments indicate that vitamin A (trans-retinoic acid) is nontoxic and may be useful for enhancing natural vaginal moisture for women suffering from atrophic vaginitis. Vitamin A increases cervical cell growth at micromolar concentrations, which could help to strengthen vaginal tissue. The presence of vitamin A increases the expression of estrogen receptor alpha, vascular endothelial growth factor and the $P2Y_2$ receptor gene in cervical epithelial cells. Such increases in expression may help to treat the symptoms of atrophic vaginitis.

Example 3

Vitamin A Increases Mucin-4 Expression

Materials and Methods

RNA was isolated (as described above) from ME-180 cervical cells treated with 0 nM or 100 nm vitamin A in the absence of serum. The RNA was reverse transcribed to form cDNA, and PCR techniques (as described above) were used to determine the effect of vitamin A on the expression of mucin-4 (MUC-4).

Results

Figure 6:
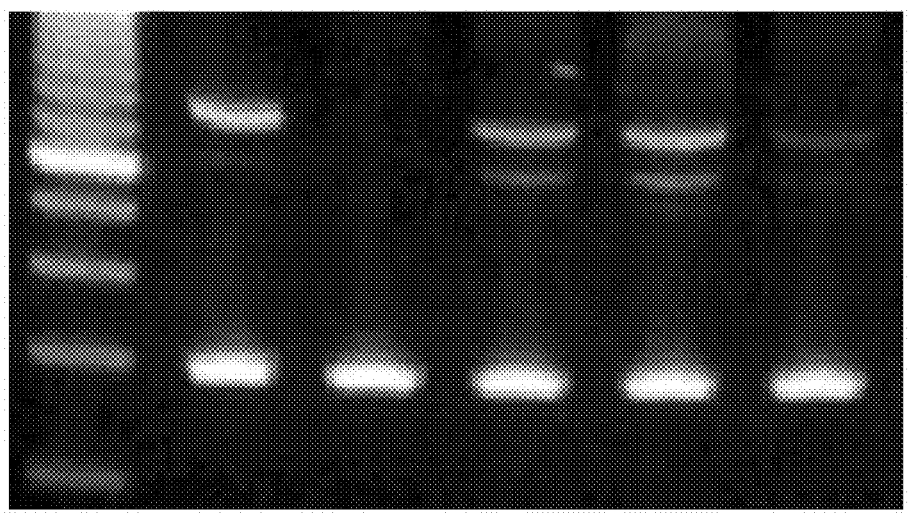
FIG. 6 provides a copy of a photograph of an ethidium bromide-stained 2% agarose gel of PCR products using RNA from various cell types as template. Lane 1 of the gel depicted in FIG. 6 contains DNA size markers, in particular a 100 bp ladder of size markers (the brightest band is 600 bp). Lane 2 contains the products of a RT-PCR reaction using template cDNA derived from cervical RNA and mucin-4 primers (800 bp product) with β-actin primers (300 bp product). Lane 3 contains the products of a similar PCR reaction using template cDNA from ME-180 cells. Lane 4 contains the products of a similar PCR reaction using template cDNA from ME-180 cells treated with 100 nM vitamin A for 24 hours.

As shown in FIG. 6, addition of control β-actin primers leads to synthesis of a 300 bp DNA product that is present in approximately equal amounts in all samples. This result indicates that approximately the same amounts of template RNA were present in all samples. However, as is also illustrated in FIG. 6, the MUC-4 product (800 bp) is found in the cervical cDNA control (lane 2). In ME-180 cells without vitamin A (FIG. 6, lane 3), the MUC-4 product is absent. However, upon addition of 100 nM vitamin A to ME-180 cells, MUC-4 expression is detectable after 4 hours or 8 hours of treatment (FIG. 6, lanes 4 and 5, respectively). After 16 hours of treatment with 100 nM vitamin A (FIG. 6, lane 6), MUC-4 expression decreases but is still detectable. These data indicate that low concentrations of vitamin A may be useful in the treatment of atrophic vaginitis by increasing the expression of MUC-4.

Example 4

Stimulation of Keratinocyte Growth

This Example provides data showing the cell proliferating effect of jasmonic acid and gibberellic acid on human skin keratinocytes.

Materials and Methods

A human skin keratinocyte cell line from Clonetics (Walkersville, Md., normal human epidermal keratinocytes, neonatal, catalog number cc-2503) was exposed to the jasmonic acid and gibberellic acid (from Sigma Chemical Co.) to determine their effect on proliferation of keratinocytes. The gibberellic acid used had the following structure (Gibberellin $A_3$).

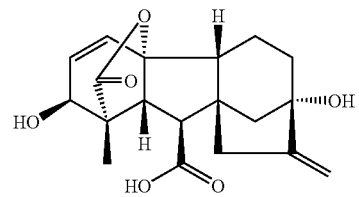

VI

The proliferative response of these human skin keratinocytes to the test compounds was measured in a 96-well assay system using keratinocyte basal medium (KBM, Clonetics, catalog number CC-3103) as a control. All compounds were tested at three concentrations, $1\times10^{-4}$ M, $1\times10^{-5}$ M and $1\times10^6$ M. Cells were seeded into a 96 well plate at a concentration of $2\times10^3$ cells in 100 µl of KBM. The plate was incubated for 24 hours at 37° C. in a humidified 5% $CO_2$ atmosphere. After incubation, 100 µl of the $1\times10^{-4}$ M, $1\times10^{-5}$ M or $1\times10^{-6}$ M solutions of jasmonic acid and gibberellic acid were added to 5 wells each. In addition, 100 µl of vehicle KBM was added to 5 wells as control. The plate was incubated for 48 hours at 37° C. in a humidified, 5% $CO_2$ atmosphere. After incubation, 20 µl of Cell Titer 96 Aqueous One Solution (Promega, Madison, Wis.) was added to all wells. The plate was swirled gently and placed back in the incubator for 3 hours. The spectrophotometric absorbance of each well was read at 490 nm.

Statistical analyses of data were performed using one-way ANOVA. $P<0.05$ is considered significant, while $P<0.0001$ is considered extremely significant and $P<0.001$ is considered as very, very significant.

Results

Table 1 illustrates the cell proliferating effect of jasmonic acid on human keratinocytes, where the concentration of jasmonic acid varied between $1\times10^{-4}$ M (designated JA4), $1\times10^{-5}$ M (designated JA5) and $1\times10^{-6}$ M (designated JA6).

TABLE 1

Effect of Jasmonic Acid on Cell Proliferation

| Group | Number of Points | Mean | Standard Deviation | Standard Error of Mean | Median |
|---|---|---|---|---|---|
| JA4 | 5 | 0.5732 | 0.02720 | 0.01216 | 0.5860 |
| JA5 | 5 | 0.7628 | 0.03805 | 0.01702 | 0.7750 |
| JA6 | 5 | 0.7734 | 0.06328 | 0.02830 | 0.7970 |
| Control | 5 | 0.5094 | 0.07334 | 0.03280 | 0.5050 |

The data provided in Table 1 indicates that jasmonic acid has strong cell proliferating activity especially at the lower concentrations ($P<0.001$ at concentrations of $10^{-5}$ and $10^{-6}$ M). The effect on cell proliferation was greater at lower, rather than higher, concentrations.

Table 2 illustrates the cell proliferating effect of gibberellic acid on human keratinocytes, where the concentration of gibberellic acid varied between $1\times10^{-4}$ M (designated GA4), $1\times10^{-5}$ M (designated GA5) and $1\times10^{-6}$ M (designated GA6).

TABLE 2

Effect of Gibberellic acid on Cell Proliferation

| Group | Number of Points | Mean | Standard Deviation | Standard Error of Mean | Median |
|---|---|---|---|---|---|
| GA4 | 5 | 0.6512 | 0.01256 | 0.005616 | 0.6510 |
| GA5 | 5 | 0.8184 | 0.04813 | 0.02152 | 0.8210 |
| GA6 | 5 | 0.7854 | 0.04743 | 0.02121 | 0.7900 |
| Control | 5 | 0.5308 | 0.06833 | 0.03056 | 0.5220 |

The data provided in Table 2 indicates that gibberellic acid has strong cell proliferating activity at all concentrations (P<0.001 at all concentrations). The effect on cell proliferation was greater at lower, rather than higher, concentrations.

Example 5

Stimulation of Collagen Production

This example provides data showing that jasmonic acid and gibberellic acid stimulate collagen production.

The stimulation response of jasmonic acid and gibberellic acid (Gibberellin $A_3$, formula V) on collagen production in the human skin fibroblast cell line (Clonetics, Walkersville, Md., normal human dermal fibroblasts, neonatal, catalog number CC-2509) was measured using Takara Biomedicals EIA assay kit (TAK MK101) sold by Panvera (Madison, Wis.). The cells were first grown in a 96-well assay system using Dulbecco's Modified Eagle's Medium (DMEM) with 10% fetal bovine serum (FBS) both purchased from Sigma Chemical Co, St. Louis, Mo. Serum-free DMEM was used as a control. All compounds were tested at three concentrations $1\times10^{-4}$ M, $1\times0-5$ M and $1\times10^{-6}$ M. Cells were seeded into a 96 well plate at a concentration of $5\times10^3$ cells in 100 µl of DMEM containing 10% fetal bovine serum (FBS, Sigma Chemical Co., St. Louis, Mo.). Plate was incubated for 24 hours at 37° C. in a humidified 5% $CO_2$ atmosphere. After incubation, the medium was aspirated and the wells were rinsed twice with 100 µl of serum-free DMEM. The final rinse was aspirated and 100 µl of the $1\times10^{-4}$ M, $1\times10^{-5}$ M or $1\times10^{-6}$ M solutions of the test compounds were added to the wells (n=2 for each concentration). In addition, 100 µl of vehicle (serum-free DMEM) was added to 4 wells as control. The plate was incubated for 48 hours at 37° C. in a humidified, 5% $CO_2$ atmosphere.

The assay was done by using the recommended 20 ul of the supernatant from each well of the 96-well plate. Standard buffer and stop solutions were freshly prepared before running the assay. 100 ul of antibody-POD conjugate solution (supplied with the kit) was added into the wells using pre antibody coated 96 well plate (supplied with the kit). 20 ul of standard and test solutions (from the other 96-well plate containing fibroblasts) were added to appropriate wells. Plate was mixed gently, sealed and incubated for three hrs. at 37° C.

After incubation each well was washed carefully four times with PBS buffer (400 ul). All the wells were completely emptied at the end of washing from any liquid.

100 ul of substrate solution (hydrogen peroxide and tetramethylbenzidine in a buffer solution, supplied with the kit) was added to each well and the plate was incubated for 15 minutes. At this point 100 ul of stop solution (freshly prepared 1N $H_2SO_4$) was added to each well in the same order as substrate. The plate was gently mixed and absorbance was read at 450 nm.

Statistical analyses of data were performed using one-way ANOVA. P<0.05 is considered significant, while P<0.0001 is considered extremely significant and P<0.001 is considered as very, very significant.

Results

Table 3 illustrates the collagen production of human fibroblast cells exposed to varying concentrations of jasmonic acid and gibberellic acid. The concentration of jasmonic acid varied between $1\times10^{-4}$ M (designated JA4), $1\times10^{-5}$ M (designated JA5) and $1\times10^{-6}$ M (designated JA6). The concentration of gibberellic acid varied between $1\times10^{-4}$ M (designated GA4), $1\times10^{-5}$ M (designated GA5) and $1\times10^{-6}$ M (designated GA6).

TABLE 3

Effect of Jasmonic Acid or Gibberellic Acid on Collagen Production by Human Fibroblasts

| Group | Number of Points | Mean | Standard Deviation | Standard Error of Mean | Median |
|---|---|---|---|---|---|
| JA4 | 2 | 0.8040 | 0.009899 | 0.007000 | 0.8040 |
| JA5 | 2 | 0.7895 | 0.006364 | 0.004500 | 0.7895 |
| JA6 | 2 | 0.7475 | 0.007778 | 0.005500 | 0.7475 |
| GA4 | 2 | 0.7780 | 0.01838 | 0.01300 | 0.7780 |
| GA5 | 2 | 0.8365 | 0.04172 | 0.02950 | 0.8365 |
| GA6 | 2 | 0.8630 | 0.008485 | 0.006000 | 0.8630 |
| CNA5 | 4 | 0.7483 | 0.006238 | 0.003119 | 0.7495 |
| Control | 4 | 0.7388 | 0.01431 | 0.007157 | 0.7330 |

The data provided in Table 3 indicate that both jasmonic acid and gibberellic acid can stimulate collagen production in human fibroblasts. The effect of gibberellic acid on collagen production was more profound, particularly at lower, rather than higher, concentrations. However, jasmonic acid strongly stimulated collagen production at higher concentrations.

Example 6

Stimulation of Fibronectin Production

This example provides data showing the effect of jasmonic acid and gibberellic acid on fibronectin production.

Materials and Methods

The stimulation response of jasmonic acid and gibberellic acid (Gibberellin $A_3$, formula V) on fibronectin production in the human skin fibroblast cell line (Clonetics, Walkersville, Md., normal human dermal fibroblasts, neonatal, catalog number CC-2509) was measured using Takara Biomedicals EIA assay kit (TAK MK115) sold by Panvera (Madison, Wis.). The cells were first grown in a 96-well assay system using Dulbecco's Modified Eagle's Medium (DMEM) with 10% fetal bovine serum (FBS) both purchased from Sigma Chemical Co, St. Louis, Mo. Serum-free DMEM was used as a control. The compounds were tested in three concentrations $1\times10^{-4}$ M, $1\times10^{-5}$ M and $1\times10^{-6}$ M in duplicate. Cells were seeded into a 96 well plate at a concentration of $1\times10^4$ cells in 100 µl of DMEM containing 10% fetal bovine serum (FBS, Sigma Chemical Co., St. Louis, Mo.). The plate was incubated for 48 hours at 37° C. in a humidified 5% $CO_2$ atmosphere. After incubation, the medium was aspirated and the wells were rinsed twice with 100 µl of serum-free DMEM. The final rinse was aspirated and 100 µl of the $1\times10^{-4}$ M, $1\times10^{-5}$ M or $1\times10^{-6}$ M solutions of the test compounds were added along with 100 µl of serum free DMEM to the wells (n=2 for each concentration). In addition, 100 µl of vehicle (serum-free DMEM) was added to 2 wells as control. The plate was incubated for 48 hours at 37° C. in a humidified, 5% $CO_2$ atmosphere.

The fibronectin assay was performed using the recommended 100 µl of the supernatant from each well of the 96-well plate. Standard buffer and stop solutions were freshly prepared before running the assay. A pre-antibody-coated 96 well plate (provided with the kit) was used to transfer the test samples and control. The plate was mixed, sealed and incubated for 1 hour at 37° C. All the wells were washed after removing sample solutions, 3 times (300 µl) with washing buffer. 100 ul of antibody-POD conjugate solution was added into the wells. Plate was mixed, sealed and incubated for one hour at 37° C. Solutions were removed and the wells were washed 3 times with washing buffer. All the wells were completely emptied at the end of washing from any liquid. 100 µl of substrate solution (hydrogen peroxide and tetramethylbenzidine in a buffered solution) was added to each well and the plate was incubated at room temperature for 15 minutes. 100 µl of stop solution (freshly prepared 1N $H_2SO_4$) was added to each well in the same order as substrate. The plate was gently mixed and absorbance was read at 450 nm.

Statistical analyses of data were performed using one-way ANOVA. $P<0.05$ is considered significant, while $P<0.0001$ is considered extremely significant and $P<0.001$ is considered as very, very significant.

Results

Table 4 illustrates the fibronectin production of human fibroblast cells exposed to varying concentrations of jasmonic acid or gibberellic acid.

TABLE 4

Summary of Data

| Group | Number of Points | Mean | Standard Deviation | Standard Error of Mean | Median |
|---|---|---|---|---|---|
| JA4 | 2 | 0.2060 | 0.002828 | 0.002000 | 0.2060 |
| JA5 | 2 | 0.2025 | 0.0007071 | 0.0005000 | 0.2025 |
| JA6 | 2 | 0.1955 | 0.0007071 | 0.0005000 | 0.1955 |
| GA4 | 2 | 0.2150 | 0.005657 | 0.004000 | 0.2150 |
| GA5 | 2 | 0.2090 | 0.004243 | 0.003000 | 0.2090 |
| GA6 | 2 | 0.2225 | 0.002121 | 0.001500 | 0.2225 |
| Control | 2 | 0.1660 | 0.004243 | 0.003000 | 0.1660 |

The concentration of jasmonic acid varied between $1\times10^{-4}$ M (designated JA4), $1\times10^{-5}$ M (designated JA5) and $1\times10^{-6}$ M (designated JA6). The concentration of gibberellic acid varied between $1\times10^{-4}$ M (designated GA4), $1\times10^{-5}$ M (designated GA5) and $1\times10^{-6}$ M (designated GA6).

Statistically all three compounds stimulated fibronectin production at all concentrations tested when compared with control. Hence, jasmonic acid and gibberellic acid are both effective for stimulating fibronectin production in human fibroblasts.

Example 7

Enhanced Human Skin Renewal

The example provides data showing that the rate of skin renewal is increased by compositions containing jasmonic acid or gibberellic acid in healthy female volunteers.

The stratum corneum renewal time is the time taken for the whole thickness of the stratum corneum to be exfoliated and replaced by new cells from the dividing epidermis. This renewal time is a fundamental indicator of skin health. Previous work has demonstrated that the turnover time of the stratum corneum can be measured non-intrusively by impregnating the skin with a fluorescent marker dye that binds avidly to the nonviable epidermal cells. See Jansen L H, Hojyo-Tomoko M T, Kligman A M., Improved fluorescence staining technique for estimating turnover of the human stratum corneum, Br J Dermatol., 90, 9-12, 1974; Ridge B D, Batt M D, Palmer H E, Jarrett A, The dansyl chloride technique for stratum corneum renewal as an indicator of changes in epidermal mitotic activity following topical treatment., Br J Dermatol., 118, 167-74, 1988; Grove G L, Kligman A M, Age-associated changes in human epidermal cell renewal., J Geron., 38, 137-142, 1983. The time required for the dye to disappear is therefore an indication of the turnover time of the stratum corneum. Therefore, any differences in the time required for the dye to disappear from treated and non-treated sites can be considered to be an expression of that product's ability to enhance epidermal renewal.

Materials and Methods

A dansyl chloride cell renewal study was conducted in healthy female volunteers ranging from 43-64 years of age. The study consisted of a two-week treatment period during which time the products were applied topically twice daily, including on weekend days, to the test sites. The area of application was designated, approximately 5 cm×10 cm on the upper inner arm. The other arm served as a control with no product application. Two compounds, jasmonic acid (JA) and gibberellic acid (GA, Gibberellin $A_3$, formula V) were separately tested at a concentration of 0.25% in hyaluronic acid (0.5% aqueous solution). Eight females received jasmonic acid and seven females received gibberellic acid.

The time required for a marker dye to disappear was used as the measure of cell renewal rate. These data are presented in Table 5.

TABLE 5

Time for Cell Renewal for Skin Treated with Jasmonic Acid (JA), Gibberellic Acid (GA) or Control

| JA PATIENT # | CONTROL (Days) | JA RENEWAL (Days) | GA PATIENT # | CONTROL (Days) | GA RENEWAL (Days) |
|---|---|---|---|---|---|
| 1 | 27 | 12 | 1 | 20 | 14 |
| 2 | 26 | 12 | 2 | 26 | 21 |
| 3 | 17 | 16 | 3 | 19 | 14 |
| 4 | 20 | 15 | 4 | 15 | 12 |
| 5 | 20 | 17 | 5 | 19 | 19 |
| 6 | 17 | 14 | 6 | 20 | 17 |
| 7 | 17 | 15 | 7 | 14 | 12 |
| 8 | 14 | 11 | | | |

Figure 7:
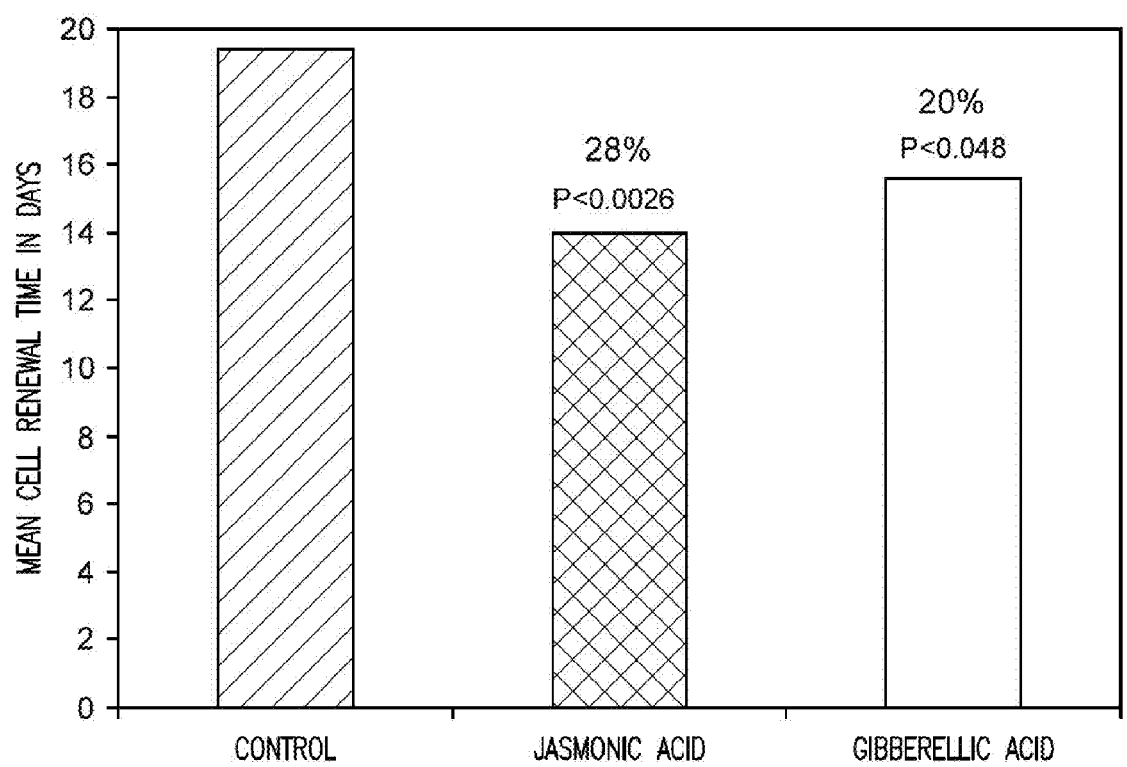
FIG. 7 graphically illustrates the effect of jasmonic acid and gibberellic acid on cell renewal time in healthy human volunteers, as compared to human volunteers that received no jasmonic acid or gibberellic acid (control). As shown, cell renewal was slower in volunteers that received no jasmonic acid and no gibberellic acid. Jasmonic acid increased the time required for cell renewal in human skin by about 28%, whereas gibberellic acid increased the cell renewal time by about 20%.

As indicated by the data in Table 5, the time required for skin cell turnover is significantly reduced when the skin is treated with compositions of either 0.25% jasmonic acid (JA) or 0.25% gibberellic acid (GA) compared to control skin that received no treatment. Jasmonic acid had an overall 28% faster cell renewal rate over control and gibberellic acid was 20% faster relative to control (FIG. 7). There was no visible sign of any skin irritation or redness in any of the study volunteers.

Compounds known as alpha hydroxy acids (e.g. glycolic acid) have been reported to decrease the cell renewal time. Moreover, treatment with alpha hydroxy acids is often accompanied by unwanted side effects such as skin irritation and redness. The compositions of the invention may satisfy an ongoing need for skin cell renewal anti-aging compositions that do not cause unwanted side effects and that are gentle to the skin.

Example 8

Jasmonic Acid Increases Epithelial Cell Growth

This Example illustrates that jasmonic acid can increase cell proliferation in a cervical epithelial cells.
Materials and Methods Human cervical epithelial cells (ME-180, ATCC) were propagated in culture at 37° C. using 5% $CO_2$ in McCoy's 5A media (Invitrogen) with 10% heat-inactivated fetal bovine serum (Invitrogen). Jasmonic acid (Sigma) was diluted in the ME-180 media to 100, 10, and 1 microgram/mL. At higher concentrations, the jasmonic acid turned the media yellow in color, indicating that the pH was too low to accomidate normal cell growth.

Figure 8:
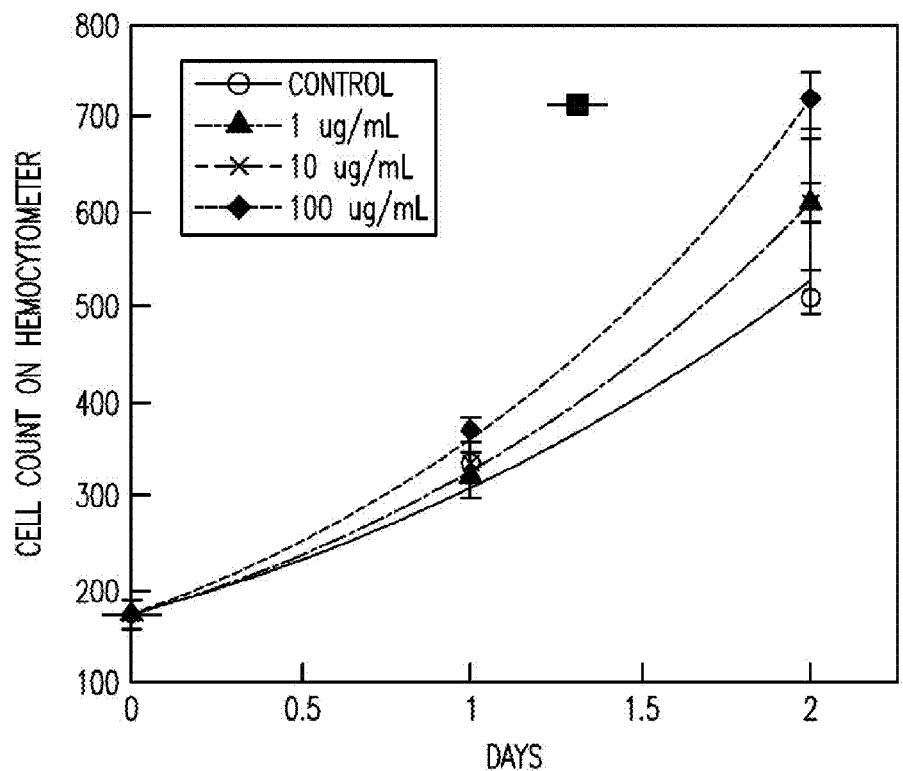
FIG. 8 graphically illustrates the effect of jasmonic acid on cell growth over time as measured by hemocytometer counting. Control cells (open circles) receiving no jasmonic acid had the least cell growth. Cells receiving 1 μg/ml jasmonic acid (closed triangles), 10 μg/ml jasmonic acid (X symbols), and 100 μg/ml jasmonic acid (closed diamonds) exhibited increased cell growth in a dose dependent manner.
Figure 9:
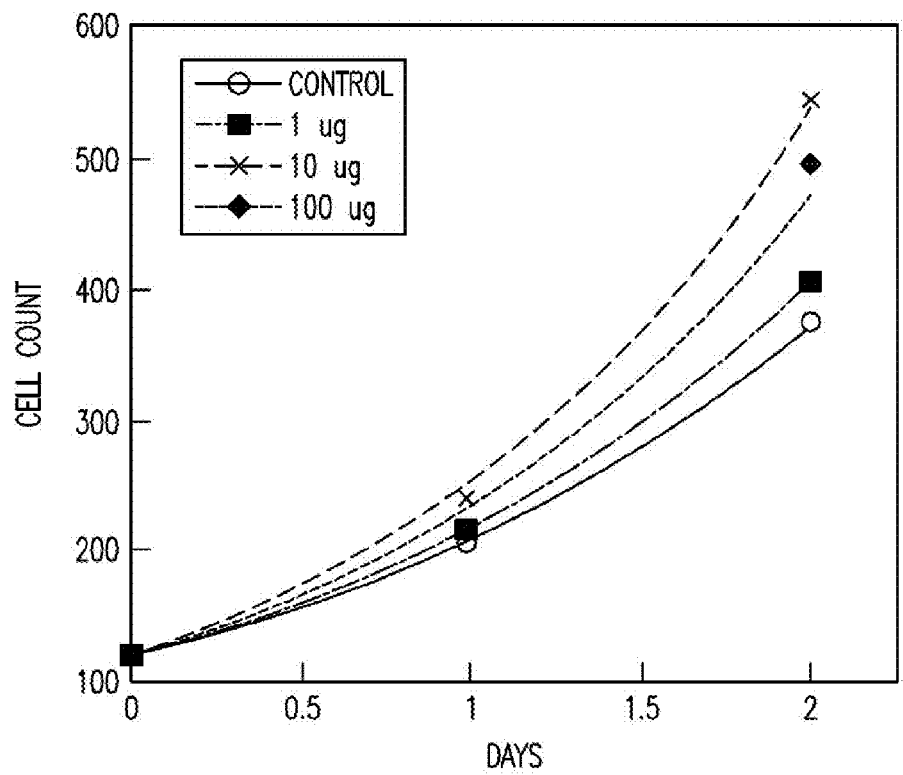
FIG. 9 graphically illustrates the effect of jasmonic acid on cell growth over time as measured by direct cell counting. Control cells (open circles) receiving no jasmonic acid had the least cell growth. Cells receiving 1 μg/ml jasmonic acid (closed squares), 10 μg/ml jasmonic acid (closed diamonds) and 100 μg/ml jasmonic acid (X symbols) exhibited increased cell growth in a dose dependent manner. These data indicate that plant hormones such as jasmonic acid can increase cell growth in epidermal cells and may be useful in treating vaginal atrophy.

ME-180 cells were plated in 12-well plates at a concentration of $5 \times 10^4$ cells per well in 2 mL of media. The cells were allowed to grow for 1 day. Cells in three wells were counted by trypsinizing and using a hemocytometer to determine cell number on day zero. The media was removed from all other wells and was replaced with fresh media, 100, 10, or 1 µg/mL jasmonic acid-containing media (2 mL) in triplicate. Cells were counted on days 1 and 2 to determine the effect of the jasmonic acid on cell growth.
Results As shown in FIGS. 8 and 9, jasmonic acid increased epithelial cell growth after two days of incubation. Therefore, jasmonic acid, as well as other plant hormones, may be useful in the treatment of atrophic vaginitis.

REFERENCES

These references and the other references cited herein are incorporated by reference in their entirety.
U.S. Pat. No. 6,264,975 entitled, "Methods of hydrating mucosal surfaces."
U.S. Pat. Nos. 5,981,506; 5,972,904; 5,958,897; 5,789,391 entitled, "Method of treating sinusitis with UTPs and other related compounds."
U.S. Pat. No. 6,277,855 entitled, "Method of treating dry eye disease with nicotinic acetylcholine receptor agonists."
U.S. Pat. No. 6,200,981 entitled, "Pyrimidine derivatives."
U.S. Pat. No. 6,107,091 entitled, "Antisense inhibition of G-alpha-16-expression."
U.S. Pat. No. 5,837,861 entitled, "Dinucleotides and their use as modulators of mucociliary clearance and ciliary beat frequency."
U.S. Pat. No. 5,985,849 entitled, "Phosphate compounds and their use as medicaments."
U.S. Pat. No. 6,107,297 entitled, "2,4-Dithi(oxo)-pyrimidin-5-yl compounds bearing a tricyclic substituent useful as P2 purinoceptor antagonists."
Garrad, R. C., Otero, M. A., Erb, L., Theiss, P. M., Clarke, L. L., Gonzalez, F. A., Turner, J. T., Weisman, G. A. "Structural basis of agonist-induced desensitization and sequestration of the $P2Y_2$ nucleotide receptor," Journal of Biological Chemistry 1998, 273(45), 29437-29444
Gorodeski, G. I., Burfiend, P., Gan, S. U., Pal, D., Abdul-Karim, F. W. "Regulation by retinoids of $P2Y_2$ nucleotide receptor mRNA in human uterine cervical cells," American Journal of Physiology 1998, C758-C765

All patents and publications referenced or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims. As used herein and in the appended claims, the singular forms "a," "an," and "the" include plural reference unless the context clearly dictates otherwise. Thus, for example, a reference to "a host cell" includes a plurality (for example, a culture or population) of such host cells, and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed is:

1. A composition consisting essentially of
an effective amount of a vitamin E compound between about 0.0001% and about 50% by weight of the composition;
an effective amount of a jasmonic acid compound between about 0.001% and about 50% by weight of the composition;
a pharmaceutically acceptable excipient for use in a vaginal cavity of a female mammal; and from about 2% to about 50% by weight of the composition of a gibberellic acid compound; wherein
the composition is a component of a vaginal insert from which the vitamin E compound, the jasmonic acid compound, and the gibberellic acid compound are released during use.

2. The composition of claim 1, wherein the composition increases growth of epithelial or epidermal cells, increases expression of mucin-4, or promotes faster cell turnover in the vaginal cavity.

3. The composition of claim 1, wherein the vitamin E compound is a compound of formula I or formula II:

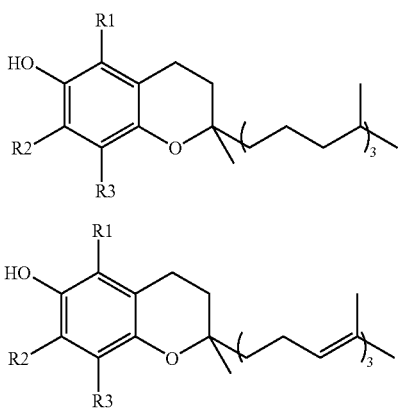

I

II wherein R1, R2, and R3 are independently hydrogen (H), methyl (CH$_3$) or hydroxyl (OH).

4. The composition of claim 1, wherein the jasmonic acid compound is a compound of formula VII, VIII, IX, or X,

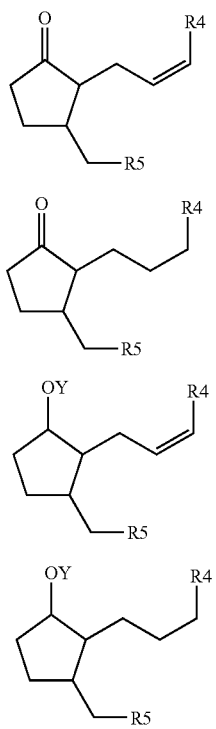

VII

VIII

IX

X wherein:
R4 is alkyl;
R5 is COOR, or —(CH$_2$)$_n$—OX, where n is an integer of from 1 to 20;
R is H, or alkyl;
X is H, or 1 to 6 hexose or pentose sugar residues; and
Y is H, alkyl, or 1 to 6 hexose or pentose sugar residues.

5. The composition of claim 1, wherein the gibberellic acid compound is a compound of formula VI, VIa, or VIb:

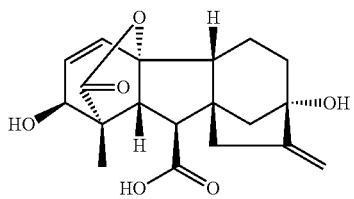

VI

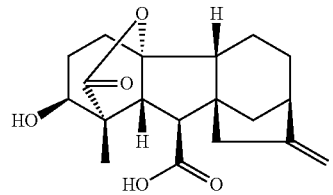

VIa

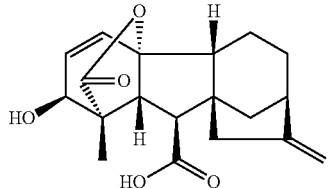

VIb

6. The composition of claim 1, wherein the vaginal insert is formed from an oleaginous base or ointment.

7. The composition of claim 1 wherein the composition includes the vitamin E compound in a concentration of from about 0.1 μM to about 1000 μM.

8. The composition of claim 1, wherein the composition includes the jasmonic acid compound in a concentration of from about 0.1 μM to about 1000 μM.

* * * * *